(12) United States Patent
Roopra et al.

(10) Patent No.: US 7,557,085 B2
(45) Date of Patent: *Jul. 7, 2009

(54) METABOLIC-BASED METHODS FOR MODULATING GENE EXPRESSION

(75) Inventors: Avtar S. Roopra, Madison, WI (US); Thomas P. Sutula, Madison, WI (US); Barry Schoenike, Belleville, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 81 days.

This patent is subject to a terminal disclaimer.

(21) Appl. No.: 11/353,368

(22) Filed: Feb. 14, 2006

(65) Prior Publication Data

US 2006/0205649 A1 Sep. 14, 2006

Related U.S. Application Data

(60) Provisional application No. 60/652,534, filed on Feb. 14, 2005.

(51) Int. Cl.
*C07K 14/00* (2006.01)
*C07H 3/00* (2006.01)

(52) U.S. Cl. .................................. 514/12; 536/1.11

(58) Field of Classification Search ........................ None
See application file for complete search history.

(56) References Cited

U.S. PATENT DOCUMENTS

| | | | |
|---|---|---|---|
| 2003/0175903 A1* | 9/2003 | San et al. | 435/90 |
| 2004/0018566 A1 | 1/2004 | Vallone et al. | |
| 2006/0088517 A1* | 4/2006 | Kriegler et al. | 424/94.61 |
| 2006/0217303 A1* | 9/2006 | Kriegler | 514/12 |
| 2006/0287253 A1* | 12/2006 | Kriegler et al. | 514/23 |

FOREIGN PATENT DOCUMENTS

WO 2005/001110 A2 1/2005

OTHER PUBLICATIONS

Bourla et al., "Age-related Macular Degeneration: A Practical Approach to a Challenging Disease", J Am Geriatr Soc. 54: 1130-1135 (2006).*
Rejdak et al., "2-Deoxyglucose enhances epileptic tolerance evoked by transient incomplete brain ischemia in mice", Epilepsy Research 43: 271-278 (2001).*
Bekierkunst A., "Nicotinamide-adenine dinucleotide in tubercle bacilli exposed to isoniazid", 152(721): 525-526 Apr. 22, 1966.*
Kuwahara et al., "The neuron-restrictive silencer element-neuron-restrictiove silencer factor system regulates basal and endothelin 1-inducible atrail natriuretic peptide gene expression in ventricular mycytoes", Molecular and Cellular Biology, American Society for Microbiology 21(6)2085-97 (Mar. 2001).
Fulco et al., SIR2 Regulates Skeletal Muscle Differentiation as a Potential Sensor of the Redox State, Molecular Cell 12(1)51-62 (Jul. 2003).
Bitterman et al., "Inhibition of Silencing and Accelerated Aging by Nicotinamide, a Putative Negative Regulator of Yeast Sir2 and Human SIRT1" Journal of Biological Chemistry 277(47)45099-107 (Nov. 2002).
Lin et al., "Calorie restriction extends yeast life span by lowering the level of NADH" Genes & Development 18(1)12-16 (Jan. 1, 2004).
Zhang et al., "Regulation of corepressor function by nuclear NADH" Science 295(5561) 1895-97 (Mar. 8, 2002).
White et al., "Mitochondrial NAD(P)H, ADP, oxidative phosphorlation, and contraction in isolated heart cells," American Journal of Physiology, Heart and Circulatory Physiology 279(4) H1849-H1857 (Oct. 2000).
Rutter et al., "Regulation of clock and NPAS2 DNA binding by the redox state of NAD cofactors." Science 293 (5529)510-514 (Jul. 20, 2001).
Mirnezami et al., "Hdm2 Recruits a Hypoxia-Sensitive Corepressor to Negatively Regulate p53-Dependent Transcription" Current Biology 13(14) 1234-1239 (Jul. 15, 2003).
Roopra et al., "Neurological disease: listening to gene silencers." Molecular Interventions 1(4)219-228 (Oct. 2001).
Fjeld et al., "Differential binding of NAD+ and NADH allows the transcriptional corepressor carboxyl-terminal binding protein to serve as a metabolic sensor," Proceedings of the National Academy of Sciences 100(16)9202-9207 (Aug. 5, 2003).
Sickmier et al., "X-ray structure of Rex-family repressor/NADH complex insights into the mechanism of redox sensing," Structure 13(1)43-54 (Jan. 2005).
Metzler et al., "High Expression of Precursor MicroRNA-155/BIC RNA in Children with Burkitt Lymphoma" Genes Chromsomes & Cancer 39:167-169 (2004).
van den Berg et al., "High Expression of B-Cell Receptor Inducible Gene BIC in all Subtypes of Hodgkin Lymphoma," Genes, Chromosomes & Cancer 37:20-28 (2003).
McManus, Michael, "MicroRNAs and cancer" Seminars in Cancer Biology 13:252-258 (2003).
Eis et al., "Accumulation of miR-155 and BIC RNA in human B cell lymphomas" PNAS 102(10)3627-3632 (Mar. 8, 2005).
Allawi et al., "Quantitation of microRNAs using a modified Invader assay," RNA 10(7)1153-1161 (2004).
Rosenwald et al., "Molecular Diagnosis of Primary Mediastinal B Cell Lymphoma Identifies a Clinically Favorable Subgroup of Diffuse Large B Cell Lymphoma Related to Hodgkin Lymphoma," Journ. of Experimental Medicine 198(6)81-862(Sep. 15, 2003).
AC002355, Birren et al., Mar. 12, 1998.
AC003688, Birren et al., Oct. 24, 1998.
AC005674, Doe Joint Genome Institute and Standford Human Genome Center, Feb. 27, 2001.
AC007536, Muzny et al., Dec. 31, 2002.
AC233331, Birren et al., Aug. 24, 2002.
AC041046, Waterston, R.H. Jul. 12, 2000.
AC068853, Birren et al., Jun. 4, 2000.
Mantis et al., "Management of multifactorial idiopathic epilepsy in EL mice with caloric restriction and the ketogenic diet: role of glucose and ketone bodies" Nutrition & Metabolism 1(11)1-11 (2004).

(Continued)

*Primary Examiner*—Anand U Desai
(74) *Attorney, Agent, or Firm*—McDonnell Boehnen Hulbert & Berghoff

(57) ABSTRACT

This invention provides methods for modulating cellular gene expression for genes operably linked to an NRSE element that is recognized by an NRSF transcriptional repressor, by changing the concentration of reduced nicotinamide adenine dinucleotide (NADH) in the cell.

4 Claims, 23 Drawing Sheets

OTHER PUBLICATIONS

Greene et al., "Caloric Restriction Inhibits Seizure Susceptibility in Epileptic EL Mice by Reducing Blood Glucose" Epilepsia 42(11)1371-78 (2001).

Belyaev et al., "Distinct RE-1 Silencing Transcription Factor-containing Complexes Interact with Different Target Genes" Joun. of Bio. Chem. 279(1)556-61 (2004).

Brown et al., "The Many HATs of transcription coactivators" TIBS 25:15-19 (Jan. 2005).

Chen et al., "NRSF/REST is required in vivo for repression of multiple neuromal target genes during embryogenesis" Nature genetics 20:136-142 (1998).

Chong et al., "REST: A Mammalian Silencer Protein That Restricts Sodium Channel Gene Expression to Neurons," Cell 80:949-957 (Mar. 24, 1995).

Douma et al., "Suppression of anoikis and induction of metastasis by the neurotrophic receptor TrkB" Nature 430:1034-1040 (Aug. 26, 2004).

He et al., "Conditional Deletion of TrkB but Not BDNF Prevents Epileptogenesis in the Kindling Model," Neuron 43:31-42 (Jul. 8, 2004).

"Finishing the euchromatic sequence of the human genome" International Human Genome Sequencing Consortium 431:931-945 (Oct. 21, 2004).

Kokaia et al., "Suppressed Epileptogenesis in BDNF Mutant Mice" Experimental Neurology 133:215-224 (1995).

Maue et al., "Neuron-Specific Expression of the Rat Brain Type II Sodium Channel Gene is Directed by Upstream Regulatory Elements".

Mazumdar et al., "Transcroptional repression of oestrogen receptor by metastasis-associated protein 1 corepressor", Nature Cell Biology 3:30-38 (Jan. 2001).

Mirnezami et al., "Hdm2 Recruits a Hypoxia-Sensitive Corepressor to Negatively Regulate p53-Dependent Transcription" Current Biology 13:1234-39 (Jul. 15, 2003).

Mori et al., "A Cell Type-Preferred Silencer Element That Controls the Neural-Specific Expression of the SCG10 Gene" Neuron 4:583-594 (Apr. 1990).

Pearse et al., "A neurotrophin axis in myeloma: TrkB and BDNF promote tumor-cell survival" Blood 105(11).

* cited by examiner

N.D=Not Detectable

SEQUENCE LISTING

<160> NUMBER OF SEQ ID NOS: 6

<210> SEQ ID NO 1
<211> LENGTH: 17
<212> TYPE: DNA
<213> ORGANISM: Artificial
<220> FEATURE:
<223> OTHER INFORMATION: NRSE consensus sequence
<220> FEATURE:
<221> NAME/KEY: misc_difference
<222> LOCATION: (10)..(11)
<223> OTHER INFORMATION: "n" can be any base
<220> FEATURE:
<221> NAME/KEY: misc_feature
<222> LOCATION: (10)..(11)
<223> OTHER INFORMATION: n is a, c, g, or t

<400> SEQUENCE: 1
ttyagmrccn nrgmsag                                                    17

<210> SEQ ID NO 2
<211> LENGTH: 22
<212> TYPE: DNA
<213> ORGANISM: Artificial
<220> FEATURE:
<223> OTHER INFORMATION: PCR primer, rat BDNF

<400> SEQUENCE: 2
gtccctggct gacactttg ag                                               22

<210> SEQ ID NO 3
<211> LENGTH: 22
<212> TYPE: DNA
<213> ORGANISM: Artificial
<220> FEATURE:
<223> OTHER INFORMATION: PCR primer, rat BDNF

<400> SEQUENCE: 3
tttctccagg actgtgaccg tc                                              22

<210> SEQ ID NO 4
<211> LENGTH: 22
<212> TYPE: DNA
<213> ORGANISM: Artificial
<220> FEATURE:
<223> OTHER INFORMATION: PCR primer, rat TrkB

<400> SEQUENCE: 4
catgggccgg cctggagttg ac                                              22

<210> SEQ ID NO 5
<211> LENGTH: 24
<212> TYPE: DNA
<213> ORGANISM: Artificial
<220> FEATURE:
<223> OTHER INFORMATION: PCR primer, rat TrkB

<400> SEQUENCE: 5
cccgttggag atgtggtgga gagg                                            24

<210> SEQ ID NO 6
<211> LENGTH: 441
<212> TYPE: DNA
<213> ORGANISM: Artificial
<220> FEATURE:
<223> OTHER INFORMATION: human snail promoter region

```
<400> SEQUENCE: 6
ggatgcccgt accttagtgg ggcttgcctg gtgtaccgca gtacccccagc ctctcaggca      60 ggtctgtggc ttggagggta cattagcatc tctgagctgc atggccactg ggaagatctc     120
tgggtccagc aaaggcagag gcctgtgaac aggattagag tcagcaccga ggacaggttt     180
ggtggccaga gcagagttca gatcgagtcc aaaaggaaga gctgagacct tggaaaatca     240
ttgccttccc acaacggtca ccagaggaag gggatgagag aagataactg aacaaagaac     300
atttatatat gttacacaaa ttatatatgc atttcatata tatatgtaat tgtgaaataa     360
tacatttttt caaaaggagc ccagagcgtg gattacagat ggctatatgc tgccagatat     420
gattgctggg gaagaactct g                                              441
```

METABOLIC-BASED METHODS FOR MODULATING GENE EXPRESSION

This application claims priority to U.S. provisional application Ser. No. 60/652,534, filed Feb. 14, 2005.

This invention was made with government support under grant No. R01-25020 by the National Institutes of Health. The government has certain rights in the invention.

BACKGROUND OF THE INVENTION

1. Field of the Invention

This invention relates to modulating gene expression associated with a disease or disorder, and identifying targets for therapeutic intervention that are genes differentially expressed in cells or tissues expressing a disease or disorder.

2. Background of the Invention

The completion of the Human Genome Project revealed the presence of about 35,000 genes in the human genome, a number smaller than anticipated (Lander et al., 2001, Nature 409: 860-921; International Human Genome Consortium, 2004, Nature 431: 931-945). As a consequence, the art has come to recognize the crucial part gene regulation plays in expressing a wide variety of phenotypes, which phenotypes may be produced by differential expression of genes in different tissues and under different developmental pathways.

The art has long recognized (see, Stent & Calendar, 1978, MOLECULAR GENETICS, 2d ed., Chapter 20, W.H. Freeman & Co.: San Francisco) the existence of cis and trans genetic elements for gene regulation, comprising genetic sequences in cis typically associated with promoter elements in one or a plurality of genes, particularly in coordinately-regulated genes, and regulatory proteins provided in trans that mediate gene regulation of promoters associated with their cognate cis elements.

In mammalian cells, one such element is a 23 base pair regulatory sequence in their promoter regions known as the Neuron Restrictive Silencing Element (NRSE)(Maue et al., 1990, Neuron 4: 223-31; Mori et al., 1990, Neuron 4: 583-94;). This element is found in the promoter regions of about 1800 genes in the mouse and human genomes (Maue et al., 1990, Id.; Mori et al., 1990, Id.; Bruce et al., 2004, Proc Natl Acad Sci USA 101: 10458-63). As a 23 base pair sequence, this element is unlikely to occur randomly, and genes with NRSEs are repressed both outside and inside the nervous system by the transcription factor Neural Restrictive Silencing Factor/Repressor of Expression of Sodium Type II (NRSF, also referred to as REST)(Chong et al., 1995, Cell 80: 949-57). Neuronal gene expression regulated by NRSF plays an important role in normal development and maintenance of neuronal phenotypes (Chong et al., 1995, Id.; Schoenherr & Anderson, 1995, Science 267: 1360-3; Chen et al., 1998, Nat. Genet. 20: 136-42; Timmusk et al., 1999, J. Biol Chem 274: 1078-84; Zuccato et al., 2003, Nat. Genet 35: 76-83), but there has been less understanding about the potential contribution of transcriptional regulation of neuronal gene expression by NRSF to pathological processes, including diseases of the nervous system and other systemic diseases.

One example of a gene regulated by NRSE/NRSF is Brain Derived Neurotrophic Factor (BDNF) and its tyrosine kinase receptor trkB (Timmusk et al., 1999, Id.). BDNF and trkB signaling have been implicated in a variety of neuronal and neural circuit phenomena in the developing and adult brain including axon sprouting, synapse formation, development of recurrent neuronal circuits that promote hyper-excitability, and long-term potentiation (LTP)(Timmusk & Metsis, 1994, Neurochem. Intl. 25: 11-15), and conditional genetic knock-outs of the NRSF target genes BDNF and trkB potently modify progression of kindling, a phenomenon of activity-dependent neural plasticity and an animal model of epilepsy (Kokaia et al., 1995, Exp Neurol 133: 215-24; He et al., 2004, Neuron 43: 31-42). In addition, recent studies have demonstrated that BDNF and trkB are also important in phenomena involving cells of epithelial origin outside the nervous system, such as the acquisition of metastatic potential and anoikis in cancer cells (Belyaev et al., 2004, J. Biol. Chem. 279: 556-561; Douma et al., 2004, Nature 430: 1034-9; Pearse et al., 2005, Blood 105: 4429-36). Potential target genes regulated by NRSE/NRSF include MDR3/MRP3 (cancer), MTA1, DCC (cancer), Netrin, beta-catenin (cancer), BDNF and TrkB (metastasis and anoikis, sleep apnea, epilepsy, pain), and atrial natriuretic peptide (cardiac hypertrophy/myocardial infarction)(Mazumdar et al., 2001, Nat. Cell Biol. 3: 30-37; Wood et al., 2003, J. Molec. Biol. 334: 863-74; Mimezami et al., 2003, Curr Biol 13: 1234-9; Bruce et al., 2004, Id.; Kim et al., 2005, Nat Struct Mol Biol 12: 423-8; Westbrook et al., 2005, Cell 121: 837-848).

A variety of metabolic intermediates act as small-molecule regulators of gene expression co-repressors and co-activators, thereby linking energy availability to chromatin structure and transcriptional output (Peterson, 2000, FEBS Lett 476: 68-72; Brown et al., 2000, Trends Biochem Sci 25: 15-9; Guarente & Picard, 2005, Cell 120: 473-82). For example, glycolysis-derived NADH is known to be an allosteric regulator of the transcriptional corepressor CtBP which suggests that CtBP could act as a redox sensor that directly integrates metabolic demands with gene expression (Zhang et al., 2002, Science 295: 1895-7). These relationships suggest a link between cellular energy states, particularly redox potential reflected in the amount of NAD and NADH in the cell, and gene expression regulation. However, there is no evidence in the art that cellular metabolism or energetics can modulate expression of NRSE/NRSF regulated genes.

There is this generally a need in the art to identify methods for modulating gene expression, particularly metabolic methods for modulating gene expression, for genes and phenotypes associated with a disease or disorder, as a way to prevent development of the disease or disorder or develop a treatment for the disease or disorder, as well as methods for identifying targets for therapeutic intervention.

SUMMARY OF THE INVENTION

This invention provides methods for modulating cellular gene expression by influencing the redox charge on a cell or tissue. One measure of redox charge in a cell or tissue is the relative concentrations of nicotine adenine dinucleotide in its oxidized (NAD+) and reduced (NADH) states. As shown in FIG. 1, two molecules of NADH are produced for every molecule of glucose consumed by glycolysis. Thus, compounds that inhibit glycolysis reduce the amount of NADH produced by a cell or tissue. Conversely, compounds that reduce depletion of NADH in a cell, such as hypoxia, increase the amount of NADH in the cell. As a consequence of changing NADH levels, gene expression for genes regulated by NRSE/NRSF-regulated promoters are repressed (or further repressed) as NADH concentrations decrease, and are de-repressed (increased or repressed to a lesser degree) as intracellular NADH levels rise. As a consequence, it is possible to modulate gene expression metabolically, and thereby achieve changes in cellular phenotype mediated by changes in gene expression. This is particularly useful for modulating gene expression related to the etiology, existence or maintenance of a number of disease states, including neurological diseases such as epilepsy, cancer metastasis, cardiac hypertrophy and myocardial infarction.

Specific preferred embodiments of the present invention will become evident from the following more detailed description of certain preferred embodiments and the claims.

DESCRIPTION OF THE DRAWINGS

An understanding of the invention is facilitated by reference to the drawings.

DETAILED DESCRIPTION OF THE PREFERRED EMBODIMENTS

This invention provides methods for modulating gene expression for genes under the transcriptional control of promoters comprising an RE1/NRSE element that is recognized by an NRSF transcription repressor. NRSE/NRSF-regulated genes are implicated in cancer metastasis, including for example MDR3/MRP3 (GenBank Accession No. M23234), MTA1 (NM_004689), DCC (NM_005215), Netrin (U75586), β-catenin (X87838), BDNF (NM_170731) and TrkB (NM_006180), neurological disorders including epilepsy (BDNF and TrkB) and cardiac hypertrophy/myocardial infarction (atrial natriuretic peptide, ANP; NM_000907). The invention thus provides methods for therapeutic intervention in a number of different diseases and disorders.

As utilized in accordance with the present disclosure, the following terms, unless otherwise indicated, shall be understood to have the following meanings.

Dietary, caloric and carbohydrate restriction has been demonstrated to be beneficial in a number of areas including longevity and neuroprotection. A recent renewed interest in "ketogenic diets" as a treatment for epilepsy has rekindled interest in the mechanism by which dietary restriction (DR) may influence neuronal activity. Reduction in reactive oxygen species and increased activity of the sirtuin class of histone deacetylases have been proposed to mediate many of the effects of DR. There is increasing evidence that dietary carbohydrate and caloric restriction moderate cellular responses to damage, alter aging processes, enhance longevity and may have therapeutic affects in neurological disorders such as epilepsy, Alzheimer's Disease and Huntington's Chorea. Significant advances have been made in understanding the mechanisms that link dietary restriction to longevity in model organisms from yeast through to mice. Reduction in reactive oxygen species levels has been implicated in decreased cellular damage allowing cells to survive longer and tolerate stress. Also, reduction in glycolytic flux and corresponding increases in the NAD:NADH ratio have been show to increase activity of the NAD dependent histone deacetylases in yeast and metazoans. These sirtuin enzymes target both chromatin and transcription factors such as p53 and the FOXO family of proteins to regulate cellular proliferation and apoptosis decisions. In a particular example, epilepsy can be advantageously treated using, for example, a "ketogenic" diet low in carbohydrates. As provided herein, epilepsy is an example of a neurological disease or disorder that can be treated metabolically, by modulating gene expression through regulation of co-repressor recruitment by NRSF to genes heavily implicated in controlling neuronal network behavior. This approach involves limiting or inhibiting glycolysis using compounds as disclosed herein including but not limited to 2-deoxy-D-glucose (2-DG).

Figure 1:
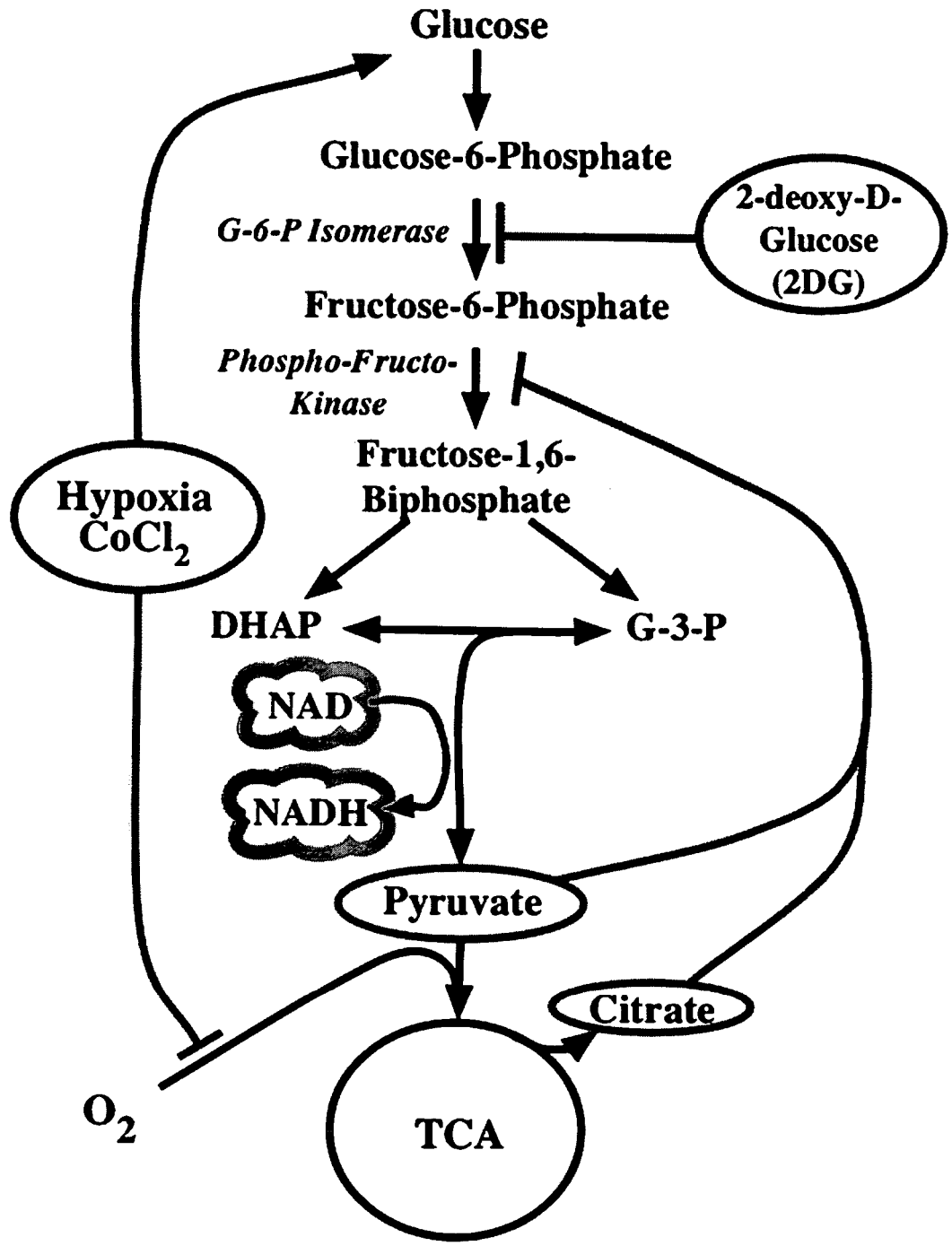
FIG. 1 is a schematic diagram of the glycolytic pathway, showing inhibition points and inhibitors, including hypoxia and $CoCl_2$ (which inhibit oxidative phosphorylation and up-regulate glycolysis, in part, by enhancing transcription of glucose transporters via the HIF1 pathway), pyruvate and citrate, which inhibit phosphofructokinase; and 2-deoxyglucose, which inhibits glucose-6-phosphate isomerase.

Glycolysis is the metabolic pathway for obtaining energy from glucose (illustrated in FIG. 1). The utilization of glucose as an energy source requires entry into the cell by specific hexose transporters, including but not limited to GLUT1 (SLC2 μl, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT 11 (SLC2A11, AP000350), GLUT11 (SLC2A11, AP000350), GLUT12 (SLCA12, AL449363), or GLUT13 (SLCA13, AJ315644). After entry into the cell, glucose is phosphorylated to form 6-phospho-glucose (6-P-G); this phosphorylation is performed by hexokinases, which are expressed ubiquitously in mammalian tissues, and glucokinases, which are expressed in liver and in some brain cells. 6-P-G is then isomerized to form 6-phospho-fructose by phosphoglucose isomerase (E.C. 5.3.1.9). This reaction requires the opening of the 5-carbon glucose ring followed by closure to form a 4 carbon ring, which occurs by oxidation of the 2 carbon hydroxyl group to a keto group. 6-phosphofructose is in turn phosphorylated to 1,6 diphosphofructose by 6-phosphofructose-1-kinase (E.C. 2.7.1.11), and this compound is cleaved to glyceraldehyde-3-phosphate and dihydroxyacetone phosphate by fructose bisphosphate aldolase (E.C. 4.1.2.13). The dihydroxyacetone phosphate formed in this reaction is converted to glyceraldehyde-3-phosphate, which is the substrate for glyceraldehyde-3-phosphate dehydrogenase (E.C. 1.2.1.12), forming 1,3 phosphoglycerate. 1,3 phosphoglycerate is converted to 3-phosphoglycerate by 3-phosphoglycerate kinase (E.C. 2.7.2.3), and the 3-phosphoglycerate product of this reaction is converted to 2-phosphoglycerate by phosphoglyceromutase (E.C. 5.4.2.1). The enzyme enolase (E.C. 4.2.1.11) converts 2-phosphoglycerate to phosphoenol pyruvate, which then forms pyruvate by the action of pyruvate kinase (E.C. 2.7.1.40). Pyruvate can then be converted to lactate or acetyl-CoA, depending on metabolic conditions in the cell.

Energy supply is critical for essential functions in all cells. Metabolism of carbohydrates and fats derived from the diet generate ATP, NADH, and FADH which ultimately provide energy for homeostatic and adaptive cellular processes that support normal physiological functions and influence responses to stress, injury, and diseases. Evidence that alterations in cellular metabolism and energy supply resulting from dietary manipulation can influence in vivo functions include the beneficial effects of calorie restriction on longevity and aging, and the observation that the so-called "ketogenic diet", which iso-calorically replaces carbohydrates with fats and proteins, can produce significant anticonvulsant effects in patients with epilepsy.

Figure 2:
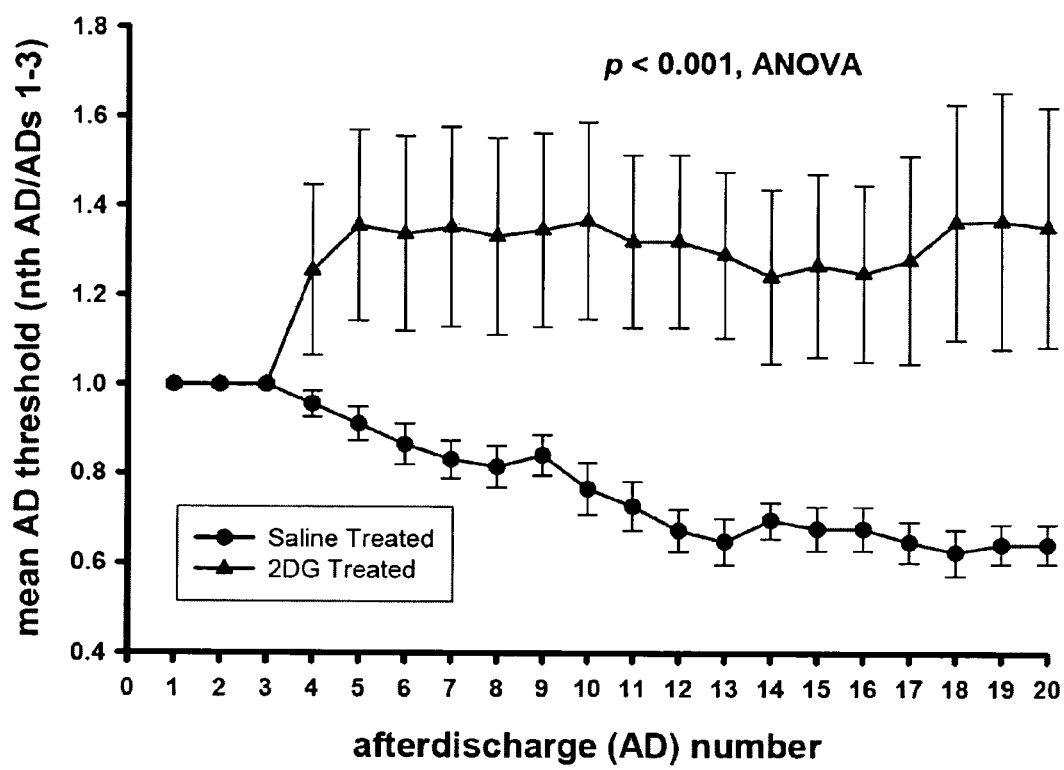
FIG. 2 illustrates the effects on after-discharge threshold of 2-DG in a mouse model of epilepsy. There was a gradual increase in the AD threshold with subcutaneous administration of 250 mg/kg 2DG prior to each kindling stimulation that evoked AD. In contrast, the control group injected with saline showed a decrease in AD as is usually observed with repeated stimuli that evoke ADs.

As disclosed herein, the use of glycolytic inhibitors to treat neurological disorders metabolically was demonstrated for epilepsy. 2-deoxy-D-glucose (2-DG), a potent inhibitor of glycolysis, was administered to rats experiencing epileptic seizures evoked by kindling, which induces seizures and long-term alterations in pathways of the hippocampal formation resembling human temporal lobe epilepsy. The effects of 2-DG on seizures evoked by kindling were examined in Sprague Dawley rats that received 2-DG and were compared to a saline-injected control group. Both groups initially received twice daily kindling stimulation (1 sec trains of 1 ms bipolar constant current pulses at 60 Hz) delivered to the perforant path input to the hippocampus according to established procedures, until 3 afterdischarges (ADs) accompanied by behavioral seizures were evoked. After the third AD, rats were randomly assigned to treatment with saline injection or 2-DG (200 mg/kg) administered subcutaneously 30 minutes prior to each kindling stimulation (see FIG. 2). The mean initial AD thresholds of the control and 2-DG treated groups did not differ. As anticipated, rats in the control group demonstrated gradual reduction in the AD threshold with repeated stimulations, consistent with the progressive features of kindling. In contrast, the AD threshold in rats treated with 2-DG gradually increased to 1500 µramps, the maximum intensity of the stimulation protocol, indicating gradually developing anti-convulsant actions of 2-DG with repeated stimulations. As the reduction of AD threshold is one measure of the progressive epileptogenic effects of kindling, the gradually increasing AD threshold in rats treated with 2-DG suggested the possibility that 2-DG was also having antiepileptogenic effects on the progressive process of kindling.

As used herein, the term "antiglycolytic compound" is intended to encompass compounds that reduce glucose metabolism, particularly in brain cells involved in epileptic or synchronized bursting or in the brains of animals suffering from a seizure disorder, preferably humans and most preferably adult or juvenile humans with epilepsy. The term specifically encompasses compounds that inhibit glycolytic enzymes, particularly hexokinase (E.C. 2.7.1.1), glucokinase (E.C. 2.7.1.2), glucose-6-phosphate isomerase (E.C. 5.3.1.9), 6-phosphofructo-1-kinase (E.C. 2.7.1.11), fructose bisphosphate aldolase (E.C. 4.1.2.13), glyceraldehyde-3-phosphate dehydrogenase (E.C. 1.2.1.12), triose phosphate isomerase (E.C. 5.3.1.1), phosphoglycerate kinase (E.C. 2.7.2.3), phosphoglyceromutase (E.C. 5.4.2.1), or pyruvate kinase (E.C. 2.7.1.40). The term also includes compounds that inhibit glucose transporter proteins, particularly glucose transporters known in the art as GLUT1 (SLC2A1, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT11 (SLC2A11, AP000350), GLUT12 (SLCA12, AL449363), or GLUT13 (SLCA13, AJ315644). In preferred embodiments, an antiglycolytic compound of the invention is 2-deoxyglucose, or a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). In additional preferred embodiments, the antiglycolytic compound is a sugar that can be metabolized into 2-DG, such as 2-deoxy-D-galactose (which is metabolized into 2-DG after phosphorylation to 2-deoxy-D-galactose-6-phosphate), and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as iodoacetate. More preferably, an antiglycolytic compound of the invention is 2-deoxy-D-glucose (2-DG), 2-deoxy-D-galactose (2-Dgal) or iodoacetate, which also inhibits enzymes of the glycolytic pathway.

The antiglycolytic compounds provided by the invention, and methods for using them to modulate gene expression as disclosed herein inhibit at least one of the enzymes that mediate glycolysis. In preferred embodiments, 2-DG inhibits conversion of 6-phosphoglucose to fructose-6-phosphate due to the lack of an hydroxyl group at the 2'-carbon position, resulting in a shutdown of the glycolytic pathway. Thus, 2-DG acts as a "low calorie mimic" because it prevents utilization of glucose otherwise present in the diet and available for metabolic breakdown. In alternative embodiments, other glycolysis inhibitors can be used, such as iodoacetate that inhibits glyceraldehyde-3-phosphate dehydrogenase (E.C. 1.2.1.12); and halogenated analogues of glycolytic intermediates, such as 1,6-dichloro-1,6-dideoxy-D-fructofuranose (dichlorodideoxyfructose, DCF), 1-chloro-3-hydroxypropanone, its dimethylketal and bromopyruvate. Other preferred embodiments are halogenated derivatives of 2-DG such as 2-fluorodeoxyglucose-D-glucose In alternative embodiments, other deoxy derivatives of hexose sugars that are useful in the practice of the methods of the invention include 2-deoxy galactose. These compounds function in a analogous manner and prevent galactose from being used as a carbon source. Alternative embodiments also include 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n), sugars that can be metabolized into 2-DG, such as 2-deoxy-D-galactose (which is metabolized into 2-DG after phosphorylation to 2-deoxy-D-galactose-6-phosphate), and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG, such as iodoacetate, formulated to be used according to the methods of the invention.

Gene expression, and changes in gene expression of certain genes is implicated in disease etiology in epilepsy and other neurological diseases. For example, BDNF and TrkB are heavily implicated in the progression of epilepsy. In a rat kindling model of epilepsy, conditional knockout of BDNF or TrkB prevents or retards progression of epilepsy. Expression of BDNF and TrkB in the hippocampus are regulated by the NRSE/NRSF repressor element/repressor system, and the expression of these genes in the hippocampus are shown herein to be metabolically regulated by compounds that inhibit glycolysis like 2-DG. Shown herein are the results of gene expression experiments surveying changes in gene expression in rat hippocampus that were associated with metabolic changes induced inter alia by treatment with 2-DG. As disclosed below, metabolic control is conferred upon neuronal genes heavily implicated in the progression of neurological disorders such as epilepsy.

In performing these gene expression experiments, conventional techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Similarly, conventional techniques may be used for chemical syntheses, chemical analyses, pharmaceutical preparation, formulation, and delivery, and treatment of patients.

As used herein, the term "gene" can comprise a native genetic sequence or other natural or synthetic, processed or unprocessed (i.e., a gene including exons and introns or a cDNA), coding or non-coding sequence.

As used herein, the term "promoters" refers to un-transcribed sequences located upstream (i.e., 5') to the translation start codon of a structural gene (generally within about 100 to 1000 bp) that control transcription of the structural gene to which they are operably linked. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no regulation of gene expression. A large number of promoters of both promoter types, recognized by a variety of potential host cells, are well known. "Transcriptionally active" promoters are those promoters that can function in a selected host cell. Factors (cis and trans) associated with mammalian promoter elements include but are not limited to the RNA polymerase holo-complex, comprising RNA polymerase II (RNAPII), and transcription factors TFIIB, TFIIE, TFIIF, TFIIH, SWI/SNF and SRB/MED; chromatin comprising nucleosomes made up of histones that condense DNA; the consensus TATA sequence; upstream repressor sequences (URSs) associated with generic repressor molecules, assisted by co-repressors SIN3, RPD3, SSN6 and TUP1; and upstream activator sequences (UAS) associated with activator molecules.

As used herein, the term "operably linked" refers to components such as genetic components that are in a relationship, specifically covalently linked to one another, permitting them to function in their intended manner. For example, a control sequence "operably linked" to a protein coding sequence is ligated thereto so that expression of the protein coding sequence is achieved under conditions compatible with the transcriptional activity of the control sequences. In particular, a transcriptionally-regulated promoter is covalently linked in an orientation, typically 5' to an open reading frame encoding an amino acid sequence of a protein, such as a reporter gene or a fusion protein of the invention, so that transcription of the coding sequence is appropriately regulated.

The term "endogenous" as used herein refers to genomic material that is not exogenous, that is, which has not been introduced into the cell. Such endogenous genomic material usually develops within an organism, tissue, or cell and is not inserted or modified by recombinant technology. Endogenous genomic material encompasses naturally occurring variations.

The term "exogenous", "foreign", or "heterologous" as used herein refers to genomic material that is not endogenous, that is, material that has been introduced into the cell. The terms can also encompass a chimeric protein or gene sequence, or a complementary configuration of non-functional fragments from different proteins that together restore a detectable degree of activity of the native protein. Typically such material is inserted or modified by recombinant technology.

As used herein, the term "genetically modified" refers to an organism whose genome has been modified by methods including the non-limiting examples of addition, substitution, or deletion of genetic material. Such methods of genetic manipulation are well known in the art and include, but are not limited to, random mutagenesis, point mutations, including insertions, deletions, and substitutions of one or a plurality of individual nucleotide residues, knock-out technology, and transformation of an organism with a nucleic acid sequence using recombinant technology, including both stable and transient transformants.

As used herein, the term "reporter gene sequence" refers to genetic material that encodes a protein that has an effect or produces a gene product that is itself detectable or that can produce a detectable reaction product. In an embodiment, the reporter gene sequence is required for survival and growth of a host cell grown in a selective culture medium. Non-limiting examples of such reporter genes encode proteins that (a) confer resistance to antibiotics or other toxins, e.g., zeocin, ampicillin, tetracycline, methotrexate, neomycin, or kanamycin for host cells; (b) complement auxotrophic deficiencies of the cell, such as leu2 or his deficiency in yeast; or (c) supply critical nutrients not available from complex media. Preferred reporter gene sequences encode proteins capable of being detected and include the non-limiting examples of drug resistance (e.g., ampicillin, kanamycin, chloramphinicol, zeocin, neomycin, G418, hygromycin, and the like), enzyme activity (e.g., peroxidase, lactamase, dihydrofolate reductase (DHFR), and the like), fluorescence or phosphorescence (e.g., luciferase, green fluorescent protein, and the like), specific binding pairing (e.g., antibodies, functional antibody fragments, ligands and receptors, and the like), localization signals (e.g., Tat, pelB, and the like), and phenotype selection (e.g., growth on particular media, such as an amino acid auxotrophy). In a most preferred embodiment the reporter gene sequences encode proteins including but not limited to Tat, pelB, β-lactamase, green fluorescent protein, luciferase, dihydrofolate reductase (DHFR), split complementary fragments thereof, and fragments thereof that require complementation from a heterologous gene for detection.

A detectable reporter gene as used in these methods is any that is detectable, for example visibly, by the presence of the gene product. Examples of selectable reporter genes include but are not limited to green fluorescence protein (GFP), cyan fluorescence protein (CFP), yellow fluorescent protein (YFP), the red fluorescent protein DsRed, beta-glucoronidase, luciferase, and lacZ (encoding beta-galactosidase).

The recombinant expression constructs of the invention are also advantageously provided wherein a reporter gene is operably linked to the genetically-engineered promoter of the invention. Suitable reporter genes include but are not limited to luciferase, beta-galactosidase, dihydrofolate reductase, thymidine kinase, chloramphenicol acetyl transferase, green fluorescent protein, hygromycin resistance, P-glycoprotein, neomycin resistance or any other gene whose expression provides a suitable means for phenotypic selection. Reporter-gene encoding recombinant expression constructs are useful, inter alia, for optimizing expression regulation by small molecule regulators, particularly NRSE/NRSF-regulation.

A selectable reporter gene as used in these methods is any that can be used to, for example, enable or prevent the growth of a cell expressing said gene. Examples of selectable reporter genes include but are not limited to HIS3, ADE2, ADE5, ADE7, LYS2, LEU2, URA3, TRP1, KAN, NEO (neomycin resistance for growth in G-418), growth on hypoxanthine-aminopterin-thymidine (HAT) media for thymidine kinase, growth in the presence of pyrimidine analogs such as bromodeoxyuridine (BrdU) for thymidine kinase activity, and growth in methotrexate for dihydrofolate reductase (DHFR). The detectable reporter gene or genes utilized may not be the same gene or genes utilized as the selectable reporter gene (i.e., a gene required for growth). In another embodiment of this aspect of the inventive methods, protein-protein interaction is detected by reporter gene activity. Reporter gene activity may be determined by growth (i.e., using a selection protocol), or biochemical activity, or a biophysical signal such as fluorescence, photon emission, change in color spectrum, transfer of radioactive groups, or by binding to an antibody and detected either directly or indirectly, for example, by conjugation to a detectable marker such as horseradish peroxidase or a fluorescent agent.

The expression of all selectable or detectable reporter genes is dependent on the activation of upstream promoters. Upstream promoters have required DNA sequence(s) for binding transcriptional activator(s) or a site-specific DNA-binding domain that is fused to a transcription activation domain, for example, the Gal4p transcriptional activation domain and, optionally, for binding a transcriptional inhibitor directly. Transcription of selectable or detectable reporter genes is dependent on binding of transcriptional activators and repressors, such as the NRSE/NRSF-regulated promoters.

The term "detectable" refers herein to the ability to identify, measure, or localize a protein product, either antigenically, immunologically or enzymatically within the host cell or cell extracts. Protein products can further comprise additional sequences useful for promoting identification or purification of the protein, such as epitope or fluorescent tags. Examples of such epitope and fluorescent tags include, but are not limited to FLAG (Sigma Chemical, St. Louis, Mo.), myc (9E10) (Invitrogen, Carlsbad, Calif.), 6×-His (Invitrogen, Carlsbad, Calif.; Novagen, Madison, Wis.), HA (Boehringer Manheim Biochemicals, Indianapolis, Ind.), green fluorescent protein (GFP)(Clontech Laboratories, Inc., Mountain View, Calif.), cyan fluorescent protein (CFP)(Clontech Laboratories, Inc.), and the red fluorescent protein DsRed (Clontech Laboratories, Inc.). In one embodiment, polypeptide sequences, or fragments thereof, are operatively linked to a nucleic acid sequence encoding an "epitope tag", so that the protein is expressed with an epitope tag. The epitope tag may be expressed as the amino terminus, the carboxyl terminus, or internal to any of the polypeptide chains comprising any of said first protein second protein, or Gal80p so long as the resulting protein remains functional and is able to interact with other proteins.

Useful tools for assaying gene expression and changes in gene expression induced by metabolic changes such as treatment with 2-DG are microarray assays of mRNA from a cell or tissue such as rat hippocampus. As used herein, the terms "microarray," "bioarray," "biochip" and "biochip array" refer to an ordered spatial arrangement of immobilized biomolecular probes arrayed on a solid supporting substrate. Preferably, the biomolecular probes are immobilized on second linker moieties in contact with polymeric beads, wherein the polymeric beads are immobilized on first linker moieties in contact with the solid supporting substrate. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors). Useful microarrays for detecting differential gene expression between chemotherapeutic drug sensitive and resistant neoplastic cells are described, inter alia, in U.S. Pat. No. 6,040,138 to Lockhart et al. (commercially-available from Affymetrix, Inc., Santa Clara, Calif.) and U.S. Pat. No. 6,004,755 to Wang (commercially-available from Incyte Inc., Palo Alto, Calif.) and are also commercially available, inter alia, from Research Genetics (Huntsville, Ala.).

Gene expression profiles for each tissue can be determined by gene array analysis using gene probes derived from known genes and expressed sequence tags (ESTs). Any method that will determine any characteristic of a gene can be used so long as that characteristic can be utilized to distinguish one type of tumor from another. However, alternative methods can also be used to determine gene expression profiles. These methods include, inter alia, Southern blot and northern blot hybridization, optionally in conjunction with polymerase chain reaction (PCR) or reverse-transcription (RT)-PCR, conventionally performed using radioactive detection methods for measuring gene expression levels. In addition, other types of gene profiles instead of expression profiles can be used to identify and classify tumor samples. These alternative gene profiles include but are not limited to gene activation, or (transcription or translation) inhibition, or type and level of chemical modification of a gene, such as methylation or acetylation, that alter expression levels.

Gene arrays or microarrays as known in the art are useful in the practice of the methods of this invention. See, for example, DNA MICROARRAYS: A PRACTICAL APPROACH, Schena, ed., Oxford University Press: Oxford, UK, 1999. As used in the methods of the invention, gene arrays or microarrays comprise of a solid substrate, preferably within a square of less than about 10 microns by 10 microns on which a plurality of positionally-distinguishable polynucleotides are attached. These probe sets can be arrayed onto areas of up to 1 to 2 $cm^2$, providing for a potential probe count of >30,000 per chip. The solid substrate of the gene arrays can be made out of silicon, glass, plastic or any suitable material. The form of the solid substrate may also vary and may be in the form of beads, fibers or planar surfaces. The polynucleotides are attached to the solid substrate using methods known in the art (Schena, Id.) at a density at which hybridization of particular polynucleotides in the array can be positionally distinguished. Preferably, the density of polynucleotides on the substrate is at least 100 different polynucleotides per $cm^2$, more preferably at least 300 polynucleotides per $cm^2$. In addition, each of the attached polynucleotides comprises at least about 25 to about 50 nucleotides and has a predetermined nucleotide sequence. Target RNA or cDNA preparations are used from tumor samples that are complementary to at least one of the polynucleotide sequences on the array and specifically bind to at least one known position on the solid substrate.

This invention provides methods for effecting gene expression metabolically, for example by inhibiting glycolysis with compounds such as 2-deoxy-D-glucose. As shown herein, metabolic regulation is targeted at genes whose transcription is regulated by the NNRSE/NRSF transcription repressor cognate pair. The NRSE regulatory element is characterized by a 23-basepair consensus sequence (TTYAGMRCCN-NRGMSAG, where Y=C or T; M=A or C; R=A or G; S=C or G; and N=any base; SEQ ID NO. 1) found in the promoters of 1800 human genes. This element is recognized by a cognate factor, NRSF comprising a complex with G9a, CoREST, HDAC, POA-like and SOX-like factors, which when it binds to the NRSE represses transcription from the adjacent promoter and condenses adjacent chromatin through histone deacetylation and methylation at Lysine[9] of histone H3. The amino terminus of the NRSF forms a complex with HDAC, RbAP48, SAP30, SAP18 and SIN3.

The present invention specifically provides 2-deoxy-D-glucose (2-DG) and pharmaceutical formulations thereof to modulate gene expression for treatment of a variety of diseases and disorders related to modulation in gene expression in genes regulated by NRSE/NRSF, including inter alia as an anticonvulsant and antiepileptic agent for the treatment of seizures, epilepsy and other paroxysmal alterations in neurological and neuropsychiatric dysfunction.

2-DG is known in the art and itself and derivatives thereof have been used medicinally, particularly as a radiolabeled tracer molecule in positron emission tomography (PET) scans of myocardium for diagnosing ischemic heart disease and brain seizures in humans, as well as certain malignancies (see www.fda.gov/cder/regulatory/pet/fdgoncologyfinal.htm, visited Dec. 23, 2003). 2-DG has also been used in the art as an adjuvant to chemotherapy and as a chemotherapeutic agent per se. Maschek et al., 2004, *Cancer Res.* 64: 31-34; Aft et al., 2004, *Brit. J Cancer* 87: 805-812. 2-DG has also been used as a chemotherapeutic agent against breast cancer (Kaplan et al., 1990, *Cancer Research* 50: 544-551).

As provided herein, pharmaceutical compositions comprising 2-DG and methods using said compositions will be understood to encompass preparations of 2-deoxyglucose as the D-stereoisomer, as well as racemic mixtures thereof comprising any combination of D- and L- 2-deoxyglucose, provided that the percentage of the D-stereoisomer is greater than zero. 2-DG is available commercially, and preferably is produced according to the standards and guidelines of the pharmaceutical industry and in compliance with all relevant regulatory requirements. 2-DG can also be synthesized using methods well-established in the art (see, for example, THE MERCK INDEX, 12*th* Ed., Monograph 2951, New Jersey: Merck & Co., 1997; Bergmann et al., 1922, *Ber.* 55: 158; Snowden et al., 1947, *JACS* 69: 1048; Bolliger et al., 1954, *Helv. Chim. Acta* 34: 989; Bolliger, 1962, "2-Deoxy-D-arabino-hexose (2-Deoxy-d-glucose)," in METHODS IN CARBOHYDRATE CHEMISTRY, vol. 1, (Whistler & Wolfram, eds.), New York Academic Press, pp. 186,189).

As used herein, an "effective amount" or "therapeutically effective amount" of an antiglycolytic compound is defined as an amount that when administered to an animal, preferably a human, more preferably a human having a seizure disorder including both adults and juvenile humans with epilepsy, reduces the frequency, duration or severity of seizures experienced by the individual. The "effective amounts" of said antiglycolytic compounds are those doses that produce sub-nanomolar to millimolar concentrations of a compound such as 2-DG in blood or plasma, and will depend on species, pharmacokinetics, and route of administration.

Pharmaceutical compositions of the compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compounds of the present invention in a local rather than systemic manner, for example, via injection of the compound directly into a specific tissue, often in a depot or sustained release formulation.

Pharmaceutical compositions for use in accordance with the methods of the present invention thus can be formulated in conventional manner using one or more physiologically acceptable carriers comprising excipients and auxiliaries that facilitate processing of antiglycolytic compounds into preparations that can be used pharmaceutically. Proper formulation is dependent upon the route of administration chosen.

The compounds of the present invention can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the compounds of the present invention can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

For injection, compounds of the present invention can be formulated in appropriate aqueous solutions, such as physiologically compatible buffers such as Hank's solution, Ringer's solution, lactated Ringer's solution, or physiological saline buffer. For transmucosal and transcutaneous administration, penetrants appropriate to the barrier to be permeated are used in the formulation. Such penetrants are generally known in the art.

For oral administration, compounds of the present invention can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, antiglycolytic compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation compounds of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

In addition to the formulations described previously compounds of the present invention can also be formulated as a depot preparation. Such long acting formulations can be administered by implantation (for example subcutaneously or intramuscularly) or by intramuscular injection. Thus, for example, the antiglycolytic compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for hydrophobic embodiments of the compounds of the present invention is a co-solvent system comprising benzyl alcohol, a nonpolar surfactant, a water-miscible organic polymer, and an aqueous phase. The co-solvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems can be employed. Liposomes and emulsions are well known examples of delivery vehicles or carriers for hydrophobic drugs. Certain organic solvents such as dimethylsulfoxide also can be employed, although usually at the cost of greater toxicity.

Additionally, compounds of the present invention can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds of the present invention for a few weeks up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

The invention also provides formulations of the compounds of the present invention which as foodstuffs, food supplements or as a component of a food for an animal, preferably a human, more preferably a human with a neurological disorder such as epilepsy and most preferably adult or juvenile humans with medically-intractable or drug-resistant epilepsy, or cancer metastasis or anoikis, or cardiac hypertrophy or myocardial infarction.

For any compounds of the present invention used in the method of the invention, the therapeutically effective dose can be estimated initially from in vitro assays, as disclosed herein, or using art-recognized animal model systems or a combination thereof. For example, a dose can be formulated in animal models to achieve a circulating concentration range that includes the $EC_{50}$ (effective dose for 50% increase) as determined in vitro, i.e., the concentration of the test compound which achieves a half-maximal amount of seizure frequency. Such information can be used to more accurately determine useful doses in humans.

It will be understood, however, that the specific dose level for any particular patient will depend upon a variety of factors including the activity of the antiglycolytic compounds employed, body weight, general health, sex, diet, time of administration, route of administration, and rate of excretion, drug combination, the severity and extent of the particular seizure disorder in the patient undergoing therapy and the judgment of the prescribing physician and in particular the age of the patient, who is preferably a juvenile and more preferably pre-pubescent.

Preferred compounds of the present invention will have certain pharmacological properties. Such properties include, but are not limited to oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, *J. Chromat. B* 677: 1-27). In vitro half-lives of compounds of the present invention may be predicted from assays of microsomal half-life as described by Kuhnz and Gieschen (1998, *Drug Metabolism and Disposition*, 26: 1120-1127).

Toxicity and therapeutic efficacy of the compounds of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds of the present invention that exhibit high therapeutic indices are preferred. The data obtained from these cell culture assays and animal studies can be used in formulating a range of dosage for use in humans. The dosage of such compounds of the present invention lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch.1, p. 1).

Dosage amount and interval of administration of compounds of the present invention can be adjusted individually to reduce seizure frequency, duration or intensity. For example, doses of 250 mg/kg 2-DG or less to higher as tolerated can be used to reduce seizure frequency and minimize toxicity. Doses of as much as 2000 mg/kg 2-DG are well tolerated in rats. The anticonvulsant effects of 2-DG administered at 250 mg/kg twice daily for 3 months lasted for approximately 8 weeks after stopping 2-DG while continuing twice daily stimulation, indicating that effects of 2-DG are quite prolonged. A practitioner skilled in the art can adjust dosage in the range up to 500-600 mg/kg 2-DG and the timing of administration to produce prolonged anticonvulsant and antiepileptic effects. Efficacious dosage amounts can be adjusted to about 14 mg/kg 2-DG in children and 40 mg/kg 2-DG in adults, using therapeutic efficacy measurements (e.g., reduction in frequency or severity of seizures) as a criterion for establishing effective dosage levels.

For the embodiments such as compounds of the present invention, dosage amount and timing of administration of said compounds can be adjusted individually to provide plasma levels of the compounds which are sufficient to reduce seizure frequency, duration or intensity.

As provided herein, the methods, compounds and pharmaceutical compositions of the invention are useful in treatment of diseases and disorders of human or animal cells or tissues. Said diseases and disorders include but are not limited to neurological disorders such as epilepsy and most preferably adult or juvenile humans with medically-intractable or drug-resistant epilepsy, prevention of cancer metastasis, reduction of cardiac hypertrophy and prevention or treatment of myocardial infarction.

The Examples which follow are illustrative of specific embodiments of the invention, and various uses thereof. They set forth for explanatory purposes only, and are not to be taken as limiting the invention.

EXAMPLE 1

Neurological disorders like epilepsy, like most disorders, are associated with changes in gene expression. Many genes have been implicated in the process of epileptogenesis. For example, the TrkB receptor and its ligand, the neurotrophin Brain Derived Neurotrophic Factor (BDNF) have been shown to be essential for induction of limbic epileptogenesis by kindling.

Because epilepsy has been successfully treated in children using a "ketogenic diet" that restricts carbohydrate intake, and it has recently been shown that inhibition of glycolysis by 2-deoxyglucose (2-DG) can be used as an effective epilepsy treatment (in co-owned and co-pending U.S. patent application Ser. No. 11/155,200, incorporated by reference herein), the effects of 2-DG on TrkB and BDNF gene expression were assayed in rat brain slices.

Specifically, mRNA was extracted from hippocampus tissue from rats treated with 2-DG or untreated control rats subjected to kindling stimulation to mimic epilepsy. Quantitative Real Time PCR of reverse transcribed RNA (QRT-PCR) was performed using primers:

```
BDNF:
                                         (SEQ ID NO.2)
    5'-GTCCCTGGCTGACACTTTTGAG-3' (sense)
                                         (SEQ ID NO.3)
    5'-TTTCTCCAGGACTGTGACCGTC-3' (antisense)

Figure 3:
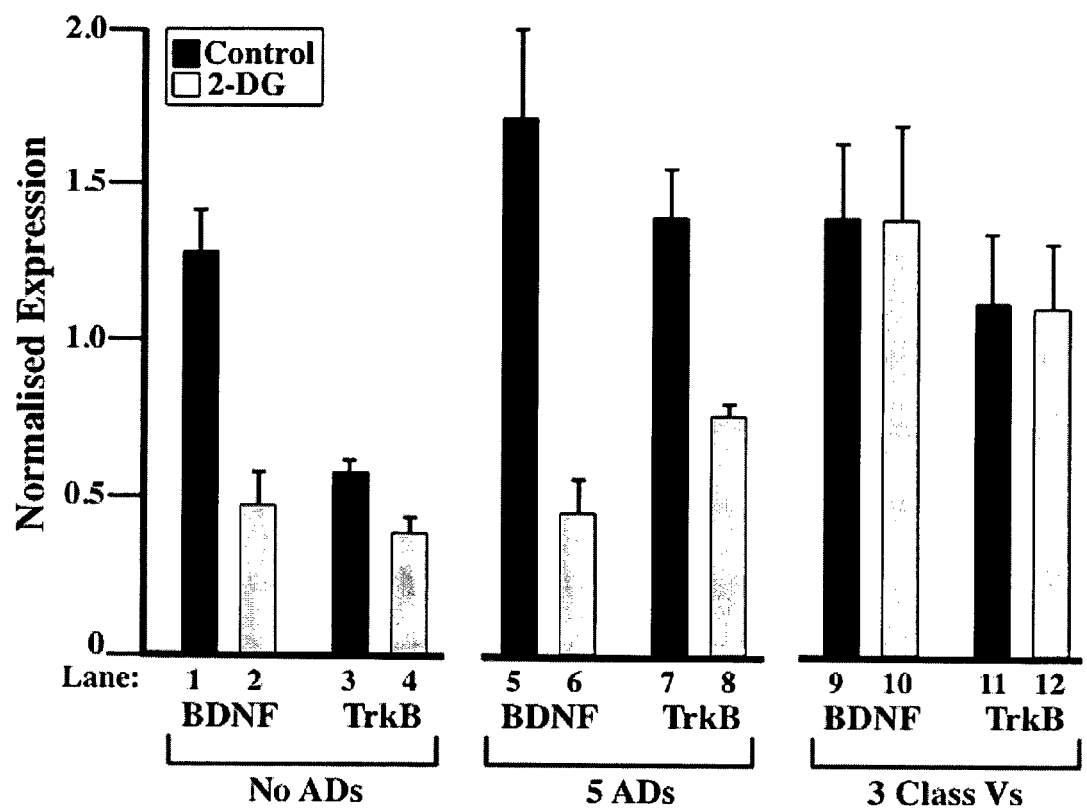
FIG. 3 shows the results of experiments described in Example 1, wherein rats administered 2-DG or saline for either 2 weeks, until the $5^{th}$ AD or $3^{rd}$ Class V seizure were sacrificed and QRT-PCR performed on hippocampal tissue with primers to BDNF, TrkB and Actin. Values plotted are BDNF or TrkB expression over Actin using rat hippocampal cDNA from an untreated rat for a standard curve.

TrkB:
                                         (SEQ ID NO.4)
    5'-CATGGGCCGGCCTGGAGTTGAC-3' (sense)
                                         (SEQ ID NO. 5)
    5'-CCCGTTGGAGATGTGGTGGAGAGG-3' (antisense)
``` and these results are shown in FIG. 3. These experiments revealed that 2DG-treated rats showed significantly reduced levels of hippocampal BDNF and TrkB expression compared to control animals (FIG. 3, lanes 1 versus 2 and 3 versus 4). The levels of actin mRNA were not affected by 2-DG treatment. Importantly, the differences in expression of BDNF or TrkB in the absence or presence of 2DG were present after 5 ADs in association with a large difference in AD threshold between 2DG-treated and control rats (FIG. 3 lanes 5 versus 6 and 7 versus 8). However there was no difference in expression in 2DG-treated and control rats that experienced 3 Class V seizures (FIG. 3 lanes 9 versus 10 and 11 versus 12). These results suggest that 2DG blocks seizure-induced increases in BDNF and TrkB expression that underlie progression to the milestone of Class V seizures. In addition, drug treatment also resulted in lowered associated histone acetylation levels for BDNF DNA.

In view of the results with BDNF and TrkB, hippocampal gene expression changes in rats treated with and without 2-DG were assessed by hybridization using microarrays (Affymetrix Rat Array (35,000 genes represented), Affymetrix, Santa Clara, Calif.). Hybridizations were performed according to the manufacturer's instructions using mRNA isolated from rat hippocampus from rats following dietary restriction or treatment with drug (2-DG). Of 35,000 genes comprising the microarray, 349 were down-regulated and 241 were transcriptionally upregulated by drug treatment. These genes are identified in Table 1, where "D" is decreased gene expression, "I" is increased gene expression, "MI" is moderately increased gene expression, and "MD" is moderately decreased gene expression. Genes of interest in disease states detected in these experiments include but are not limited to snail (NM_005985), MDR3/MRP3 (GenBank Accession No. M23234), MTA1 (NM_004689), DCC (NM_005215), Netrin (U75586), and β-catenin (X87838)(metastasis); BDNF (NM_170731) and TrkB (NM_006180) (neurological disorders) and atrial natriuretic peptide (ANP; NM_000907)(cardiac hypertrophy/myocardial infarction).

These results indicated that metabolic changes, specifically changes in glycolysis and particularly glycolytic inhibition, could result in changes in gene expression related to development of epilepsy.

EXAMPLE 2

The results in Example 1 demonstrated that inhibiting glycolysis using 2-DG could affect expression of several genes in rat hippocampus. An analysis of these genes revealed that a subset of these genes was known to be regulated by the RE1/NRSE regulatory/inhibitory element recognized by the transcription repressor NRSF. Roopra et al., 2001, *Molecular Interventions* 1: 219-28. NRSF represses BDNF levels in normal rats and tempers peak expression levels of BDNF in rats induced to have seizures with kainic acid.

To investigate whether inhibiting glycolysis could modulate gene expression controlled by NRSE/NRSF, a plasmid (pMT-NRSF) expressing the $1^{st}$ 600 residues of NRSF (the HZ4 fragment, as disclosed in Chen et al., 1998, *Nat. Genet* 20: 136-42) fused to the gal4 DNA binding domain (pMT-gal4, as disclosed in Roopra et al., 2000, *Molec. Cell Biol* 20: 2147-57) was transfected into JTC-19 rat lung fibroblasts (a non-neuronal cell line that exhibits a robust and well characterized NRSF mediated repression; see, Bruce et al., 2004, *Proc Natl Acad Sci USA* 101: 10458-63; Roopra et al., 2004, *Id.*; Belyaev et al., 2004, *J. Biol Chem.* 279: 556-561; Wood et al., 2003, *J. Mol Biol* 334: 863-74), along with a reporter gene construct wherein luciferase was placed under the transcriptional control of a synthetic promoter comprising the promoter from the adenovirus E1b gene (including then TATA box), operably linked to RE1/NRSE sequences (Roopra et al., 2004, *Id.*) JTC-19 cells were transfected with the luciferase reporter plasmid (G5-TATA-Luc) and plasmids expressing the gal4 DNA binding domain(pMT-gal4; DBD) or gal4 fused to NRSF (pMT-NRSF) and incubated under conditions as set forth in FIG. 4 for 16 hrs.

Figure 4:
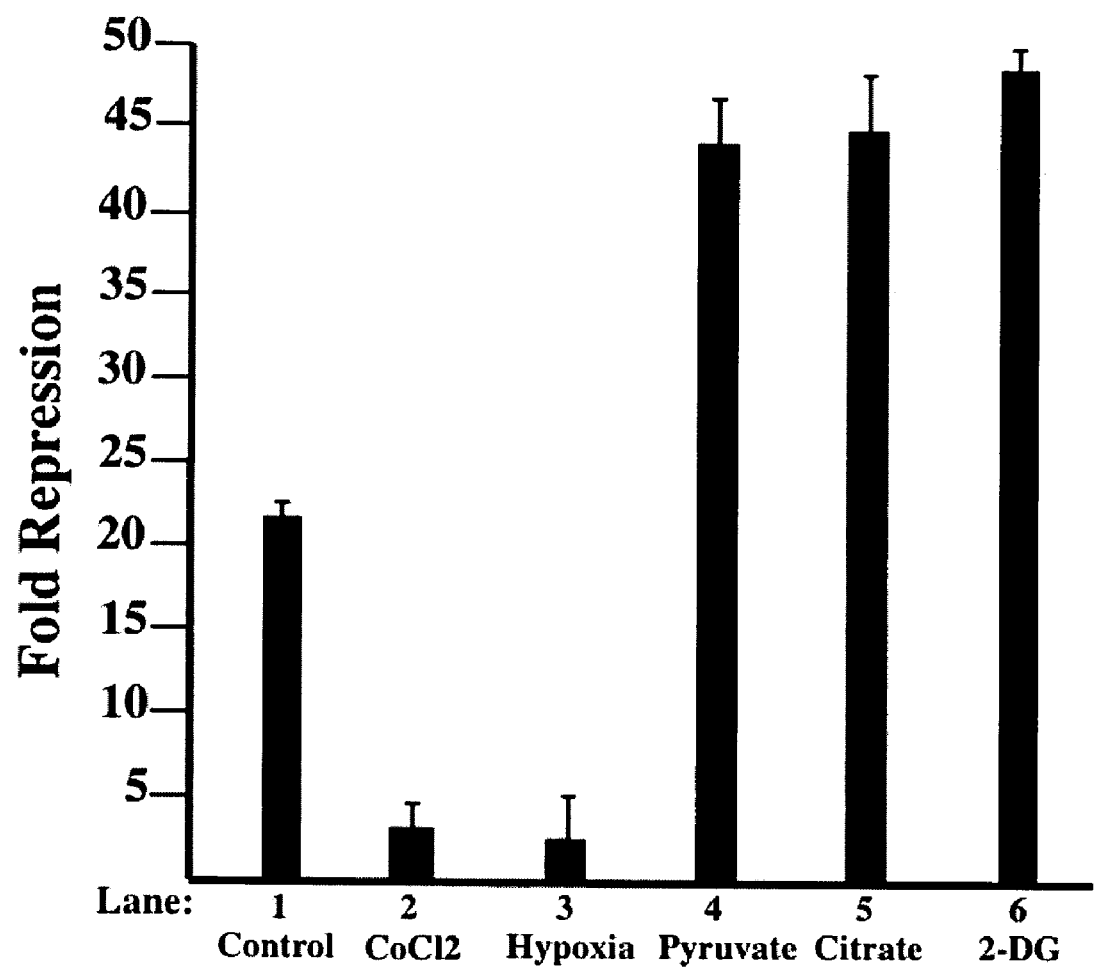
FIG. 4 is a graph showing that glycolysis regulators affect transcription regulated by NRSE/NRSF complexes, whereby pyruvate and citrate increase repression, and hypoxia and $CoCl_2$ decrease repression.
Figure 5:
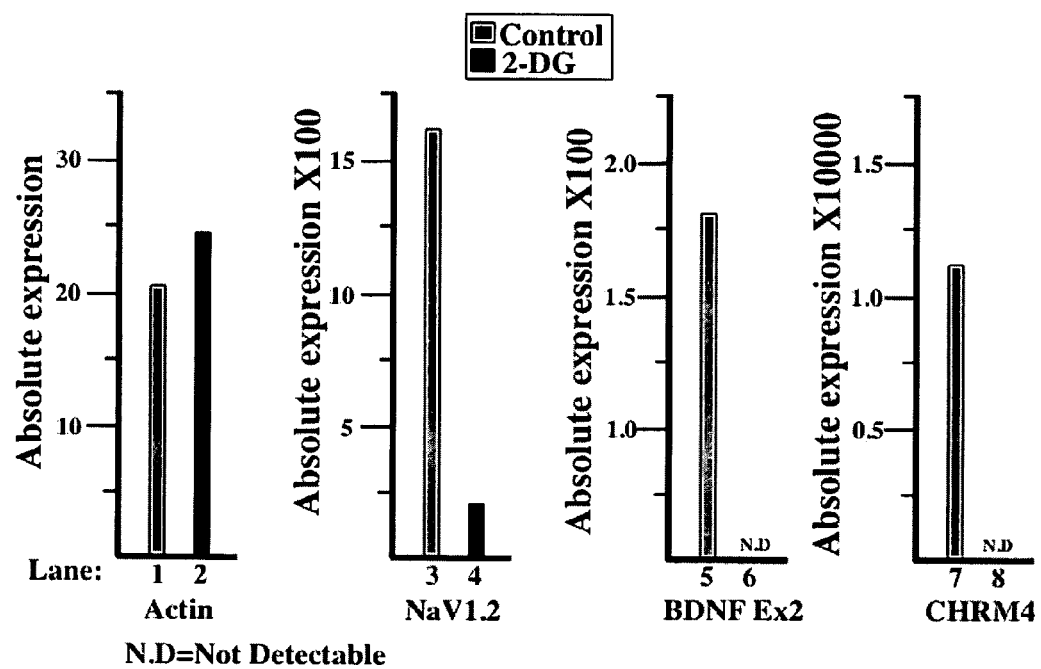
FIG. 5 are graphs showing the results of quantitative reverse-transcriptase-PCR experiments, wherein NaV1.2 is sodium type II (NaV1.2); BDNF is Brain Derived Neurotrophic Factor (BDNF) and CHRM4 is muscarinic acetylcholine receptor type 4 (CHRM4), all genes repressed by NRSE/NRSF, and actin (not an NRSF target).

These results are shown in FIG. 4, which is a graph of luciferase activity under various conditions that affect glycolysis. Firefly luciferase measurements were normalized to co-transfected pRL-TK and expressed as fold repression (gal4 DBD/gal4-NRSF). Values are the average of at least three experiments performed in triplicate. Error bars indicate standard errors. As shown in the Figure, incubating the cells in elevated concentrations of pyruvate and citrate increased repression of luciferase gene expression, whereas hypoxia and $CoCl_2$ treatment decreased repression at these promoters. These results showed that under conditions of increased glycolytic flux and reduced oxidative respiration (i.e. in the presence of $CoCl_2$ or hypoxia), NRSF mediated repression was abrogated. Conversely, addition of pyruvate or citrate (allosteric inhibitors of phosphofructokinase) or 2-DG itself to reduce glycolytic flux resulted in increased repression of reporter gene expression by NRSF. These results were consistent with the results obtained with 2-DG, that inhibition of glycolysis increased gene expression repression (i.e., expression levels decreased) and hypoxia reduced gene expression repression (i.e., expression levels increased). These results also confirmed that the molecular basis for gene expression modulation by metabolic changes in glycolysis involves the RE1/NRSE element and NRSF transcriptional repressor. Importantly, quantitative reverse-transcriptase-PCR (QRT-PCR) experiments performed as described above showed (FIG. 5) that chromosomal NRSF target genes were also repressed by 2-DG treatment in these cells, whereas actin levels were unaffected. In these experiments, cells were grown in the presence or absence of 1 mM 2-DG for 24 hrs, harvested and RNA subjected to QRT-PCR with primers to the NRSF target genes Sodium Type II (NaV1.2), Brain Derived Neurotrophic Factor (BDNF) and Muscarinic Acetylcholine Receptor Type 4 (CHRM4) or actin (not an NRSF target). Rat hippocampal cDNA was used to generate a standard curve and values plotted are microliter equivalents of hippocampal cDNA.

Figure 6:
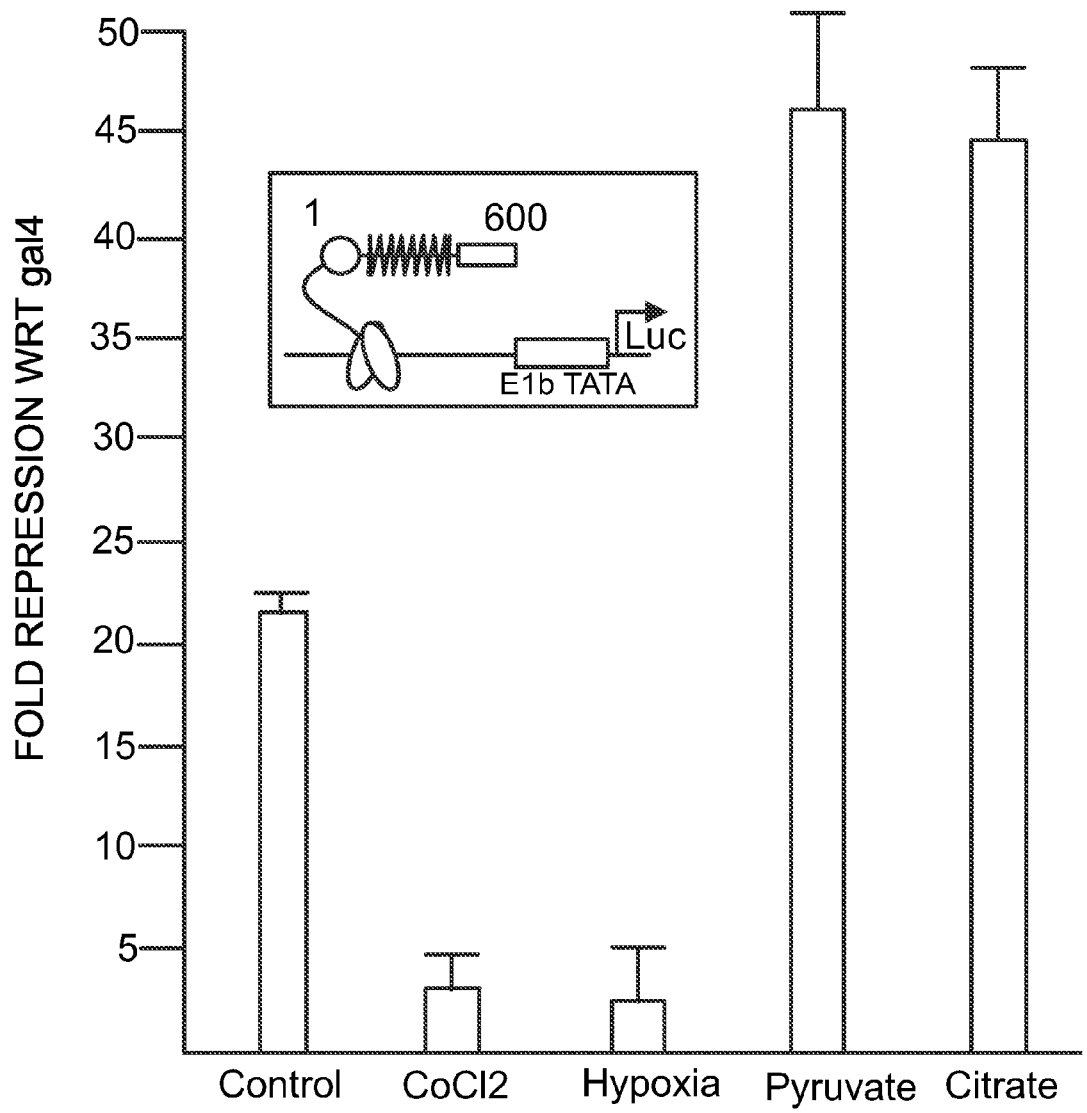
FIG. 6 is a graph showing the effects of 2-deoxyglucose (2-DG) treatment of JTC-19 rat lung fibroblasts cells on transcription of NRSE/NRSF regulated genes. The lung fibroblast cells were transfected with NRSE/NRSF regulated reporter (luciferase) gene construct (shown in the inset).

The metabolic effects of 2-DG were further investigated using this luciferase construct, and these results are shown in FIG. 6. This Figure shows a graph of the effects of 2-DG treatment of JTC-19 rat lung fibroblasts cells on transcription of the NRSE/NRSF regulated reporter (luciferase) gene construct described above. These results indicated that 2-DG increased repression by NRSF only in the presence of glucose. Addition of pyruvate to glucose also increased repression, and 2-DG augmented this effect. The results obtained by performing this experiment in the absence of glucose established that 2-DG increased repression by NRSF by inhibiting glycolysis (as compared to heightening repression due to any other biological functions of 2-DG), because 2-DG was unable to further augment repression in the absence of glucose. This result suggested that glucose was required for the 2-DG effect.

Thus, these results established that inhibition of glycolysis was responsible for the observed changes in gene expression, and that these changes were mediated by NRSE/NRSF-regulated transcriptional repression.

EXAMPLE 3

The results obtained in the experiments described in Examples 1 and 2 above established that glycolytic inhibition was capable of effecting changes in cellular gene expression. One consequence of glycolytic inhibition is to change the relative concentrations of the oxidized (NAD+) and reduced (NADH) forms of nicotinamide adenine dinucleotide.

It was recognized in the art that the transcriptional co-repressor C-terminal binding protein (CtBP) confers redox sensitivity to a number of transcription factors including ZEB (Zhang et al., 2002, *Science* 295: 1895-7) and Hdm2 (Mimezami et al., 2003, *Curr Biol* 13: 1234-9). CtBP2 binding to a number of transcription factors is regulated by NADH levels. This regulation may be due in part to the ability of CtBP2 to dimerize in the presence of the dinucleotide. This co-factor has high homology to 2-hydroxy-acid dehydrogenases and is able to bind NADH with nanomolar affinity and Kd values approximating free cellular concentrations of these dinucleotide cofactors.

The capacity for CtBP to be involved in NRSF-mediated gene repression was tested in the JTC-19 fibroblast experiments set forth in Example 2. (CtBP exists as 2 isoforms in vertebrates (CtBP1 and CtBP2), and expression of either CtBP1 or CtBP2 showed identical results (data not shown) and so all further experiments with performed with CtBP2.) In order to determine whether NRSF recruited CtBP to affect metabolic control of target genes by using NADH as an indicator of cellular redox state, JTC-19 cells were transfected with G5-TATA-Luc reporter plasmid, limiting amounts of gal4 DBD or plasmids expressing gal4-NRSF(1-600) and either wild type CtBP2 or CtBP2 bearing a point mutation ($G^{189} \rightarrow A^{189}$) in a critical glycine residue that prevents CtBP2 from binding NADH (G189A; Mimezami et al., 2003, *Id.*). Cells were either grown under normoxic or hypoxic conditions (to increase cytoplasmic/nuclear NADH levels) for 16 hrs and assayed as described above.

Figure 7A:
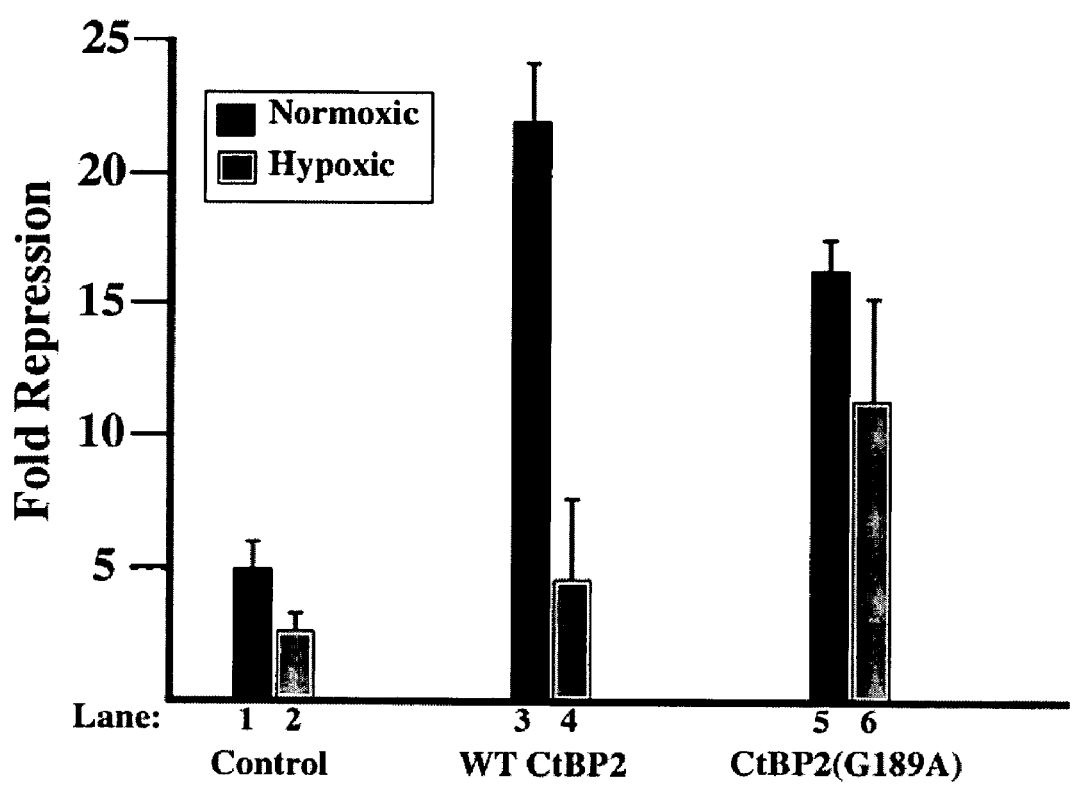
FIG. 7A shows the results of NRSE/NRSF-regulated reporter gene expression under normoxic and hypoxic conditions in cells comprising normal and mutant (NADH-non-responsive) CtBP2. In cells containing wildtype CtBP2, transcriptional repression is reduced under hypoxic conditions, wherein the amount of intracellular NADH is increased. In contrast, hypoxic conditions result in smaller changes in transcriptional repression in CtBP2(Gly$^{189}$→Ala$^{189}$). mutant-containing cells. Thus, this mutant CtBP2 remains bound to NRSF despite increasing intracellular condition of NADH, so that NRSE/NRSF-regulated gene transcription is unaffected by metabolic changes in the redox charge on the cell.

FIG. 7A shows the results of NRSE/NRSF-regulated reporter gene expression under normoxic and hypoxic conditions in cells comprising normal and mutant (NADH-non-responsive) CtBP2. Co-transfection of CtBP increased NRSF-dependent repression (compare lanes 1 and 3) and this repression was sensitive to hypoxia (compare lanes 3 and 4). In cells containing wildtype CtBP2, transcriptional repression is reduced under hypoxic conditions, wherein the amount of intracellular NADH is increased. In contrast, hypoxic conditions result in smaller changes in transcriptional repression in CtBP2 (Gly$^{189}$→Ala$^{189}$). mutant-containing cells. Thus, this mutant CtBP2 remains bound to NRSF despite increasing intracellular condition of NADH, so that NRSE/NRSF-regulated gene transcription is unaffected by metabolic changes in the redox charge on the cell. These results showing that expression of wild type CtBP2 enhanced repression by NRSF are consistent with CtBP2 acting as a corepressor for NRSF. Furthermore, this repression was sensitive to hypoxia. However, mutant CtBP2 (Gly$^{189}$→Ala$^{189}$) was able to augment NRSF mediated repression but abolished sensitivity to hypoxia. These results suggested that redox, and thus metabolic control of NRSF function is mediated by CtBP2 sensing of cellular NADH concentrations.

Figure 7B:
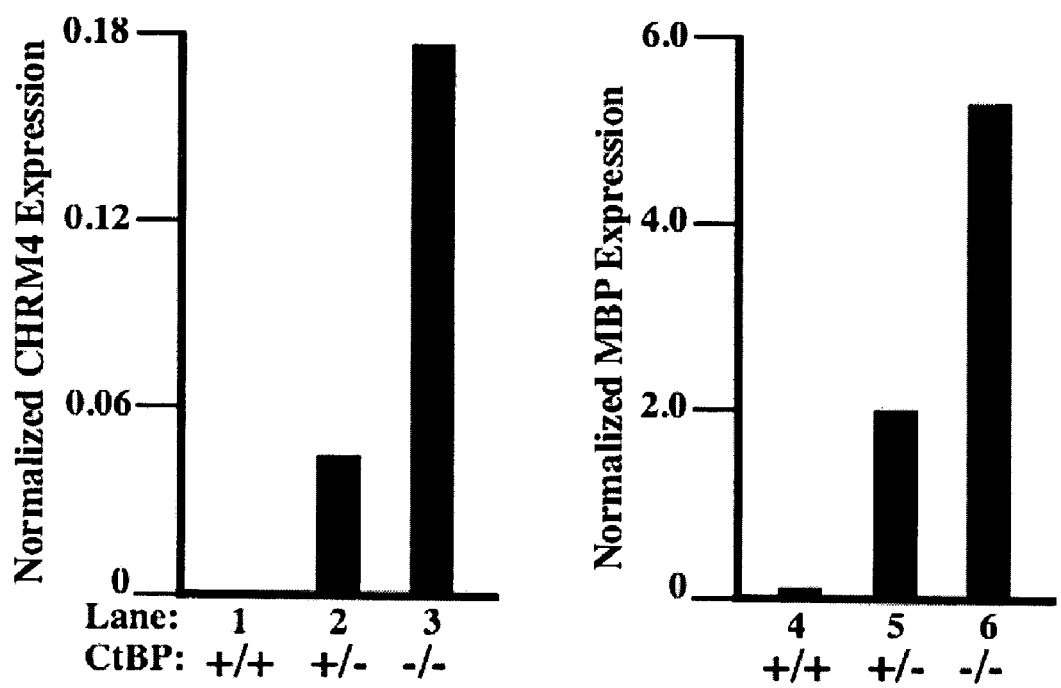
FIG. 7B is a graph of normalized CHRM4 or MBP expression in mouse embryo fibroblasts (MEFs) bearing wildtype (+/+) CtBP1 and CtBP2, or an inactivating mutation in heterozygous (–/+) or homozygous (–/–) state for both CtBP1 and CtBP2.
Figure 7C:
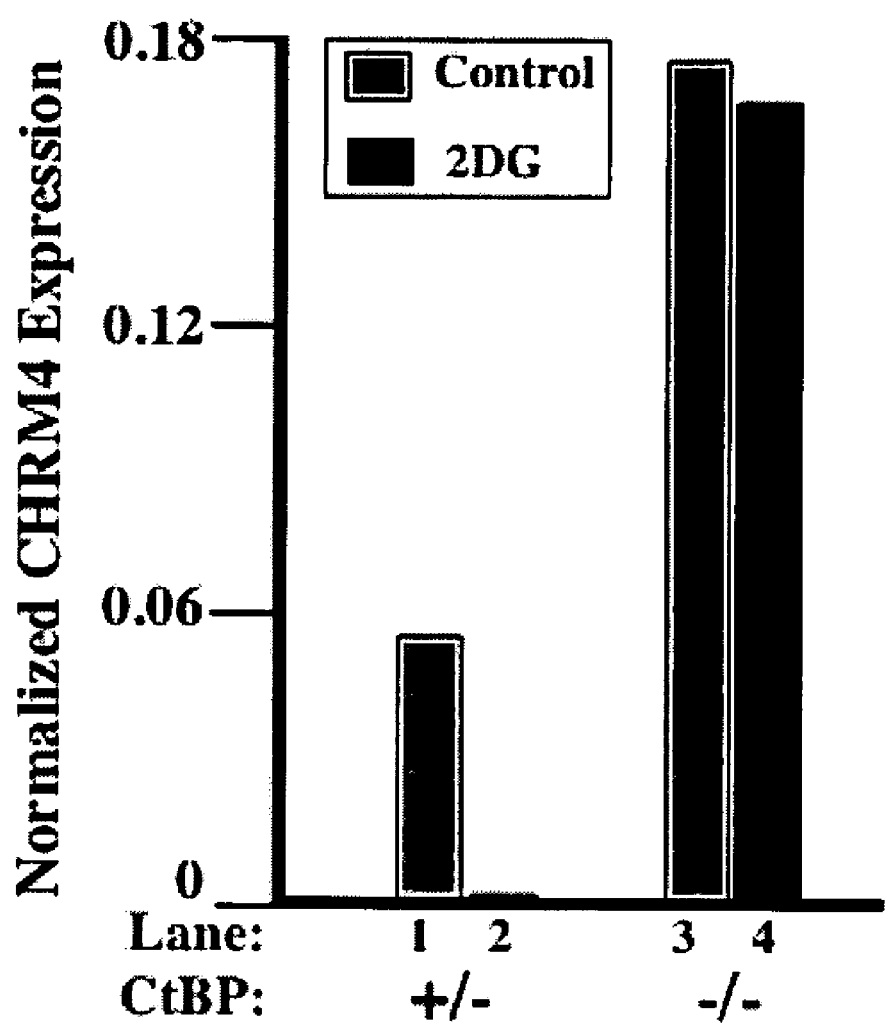
FIG. 7C is a graph of normalized CHRM4 expression in MEFs bearing an inactivating mutation in heterozygous (–/+) or homozygous (–/–) state for both CtBP1 and CtBP2, assayed in the presence of absence of 2-DG.

To test whether CtBP was required for NRSF repression of chromosomal genes, expression levels of NRSF target genes were assayed in Mouse Embryonic Fibroblasts (MEFs) heterozygous or homozygous for deletions of both CtBP1 and CtBP2 (as described in Hildebrand & Soriano, 2002, *Mol Cell Biol* 22: 5296-307). In these experiments, wild type MEFs or MEFs heterozygous (CtBP1$^{-/+}$2$^{-/+}$) or homozygous (CtBP1$^{-/-}$2$^{-/-}$) for both CtBP1 and CtBP2 mutants were analyzed for CHRM4, Myelin Basic Protein (MBP) and hypoxanthine phosphoribosyl transferase (HPRT, as a non-NRSF regulated control) expression by QRT-PCR as described in Example 2. These results are shown in FIG. 7B, plotted as CHRM4 or MBP over HPRT expression. FIG. 7B shows that NRSF target genes CHRM4 and MBP were expressed in CtBP1$^{-/+}$2$^{-/+}$ cells but not in CtBP1$^{+/+}$/2$^{+/+}$ cells. The expression levels of both genes were further elevated in CtBP1$^{-/-}$/2$^{-/-}$ cells, consistent with a dose-responsive co-repressor function for CtBP. FIG. 7C shows that in CtBP1$^{-/+}$/2$^{-/+}$ cells, CHRM4 expression was repressed upon glycolytic inhibition by growth in the presence of 1 mM 2-DG (compare lanes 1 and 2), whereas expression was not altered by 2DG in CtBP1$^{-/-}$/2$^{-/-}$ cells (shown in lanes 3 and 4). These results established that CtBP was required both for repression of chromosomal NRSF target gene expression and also for the metabolic regulation thereof, and implicated CtBP as a potential component of the regulatory mechanisms underlying the in vivo effects of 2-DG.

Immunoprecipitation experiments were performed to examine CtBP2/NRSF binding and the effect of increasing NADH concentration on such binding. In these experiments, soluble recombinant 6×-HIS-tagged CtBP2 (produced using the Qiagen Expression System, Qiagen, Valencia, Calif., according to the manufacturer's instructions) was pre-incubated with indicated concentrations of NADH and then added to immunopurified, antibody and bead bound MYC-tagged NRSF protein (Roopra et al., 2000, *Id.*) while maintaining the appropriate NADH concentration. The resulting complexes were harvested, washed and subjected to Western blot analysis with an antibody to the 6×-HIS tag on CtBP2 (Qiagen). CtBP2 binding to NRSF is abrogated in the presence of NADH, showing that the NRSF-CtBP2 interaction is sensitive to NADH concentration.

Figure 8A:
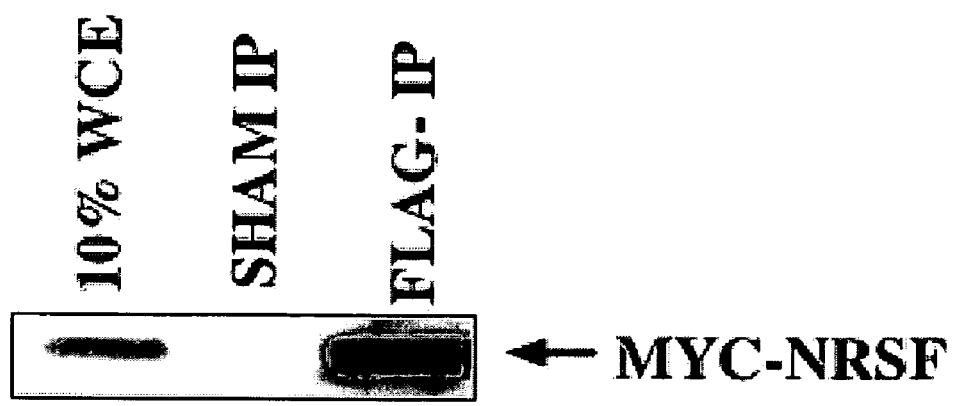
FIG. 8A shows the results of immune precipitation experiments in HEK cells were co-transfected with plasmids expressing MYC-tagged NRSF or KT3-tagged CtBP2. Protein was harvested and immunoprecipitated with anti-KT3 antibody or anti-Jun antibody as sham.

If CtBP is a redox sensitive corepressor for NRSF, then the two proteins would be predicted to interact. To test whether NRSF and CtBP2 were complexed in living cells, plasmids expressing MYC-tagged NRSF (Roopra et al., 2000, *Id.*) and KT3-tagged CtBP2 (Hildebrand & Soriano, 2002, *Mol Cell Biol* 22: 5296-307) were transfected into HEK-293 cells. Extracted protein was immunoprecipitated with anti-KT3 antibody (BD-Pharmigen, San Jose, Calif.) and subjected to Western blot (as described in Roopra et al., 2000, *Id.*) with anti-MYC antibody (9E11, Santa-Cruz Biotechnology, Inc., Santa Cruz, Calif.). FIG. 8A shows the results of immune precipitation experiments in cells expressing myc-NRSF and KT3-CtBP2 fusion proteins.

Figure 8B:
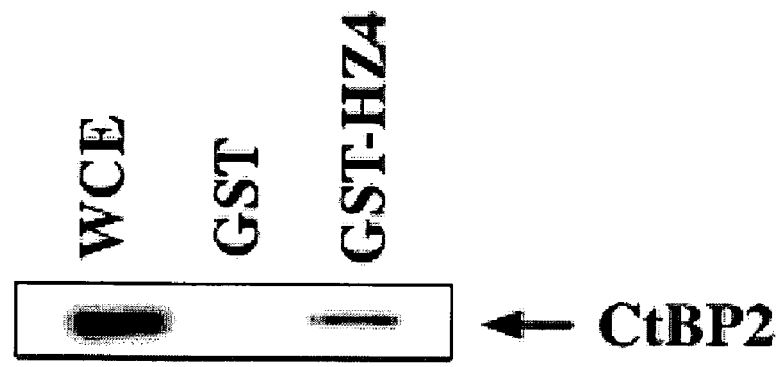
FIG. 8B shows the results of immune precipitation experiments performed using GST fused to the HZ5 fragment of NRSF and expressed in E. coli incubated with HeLa cell nuclear extract, washed and subjected to Western blot analysis with an anti-CtBP antibody (BD Pharmigen, San Jose, Calif.), where WCE represents incubation with whole cell extract (at about 1% of the amount used in the immunoprecipitation).

These results were supported by immunoprecipitation of NRSF/CtBP complex formation in vitro, wherein GST fused to the HZ4 fragment of NRSF (see above) bound purified CtBP2 expressed in *E. coli* under conditions that GST alone could not, as shown in FIG. 8B. These results demonstrated that NRSF and CtBP can form complexes in living cells and interact directly.

Figure 8C:
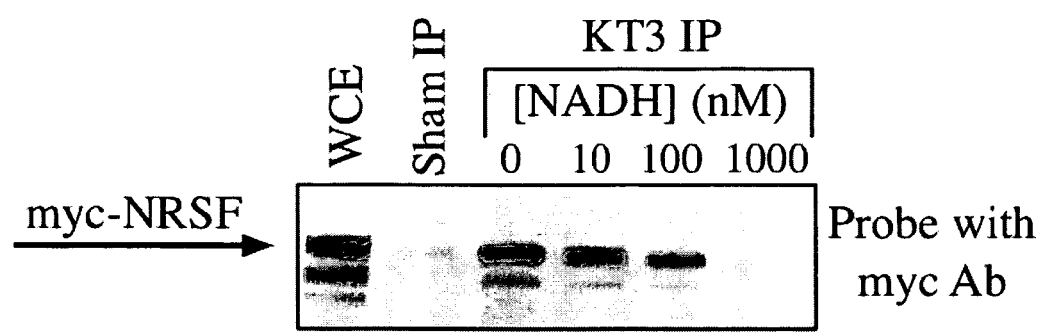
FIG. 8C shows the results of immune precipitation experiments performed on HEK cells were co-transfected with plasmids expressing MYC-tagged NRSF or KT3-tagged CtBP2. Protein was harvested, incubated with the indicated concentrations of NADH and immunoprecipitated with anti-KT3 antibody or anti-Jun antibody as sham. Immune complexes were subjected to Western blot analysis with anti-MYC antibody.

As NADH concentrations regulate CtBP2 binding to a number of transcription factors (see Zhang et al., 2002, *Id.*; Mirnezami et al., 2003, *Id.*; Kim et al., 2005, *Nat Struct Mol Biol* 12: 423-8) and the non-NADH binding G189A CtBP mutant abolishes metabolic sensitivity of NRSF function, CtBP2 binding to NRSF was tested as a function of NADH concentration. In these experiments, HEK cells were co-transfected with plasmids expressing MYC-tagged NRSF or KT3-tagged CtBP2 as described above. Protein was harvested, incubated with NADH at concentrations from 0-1000 nM and immunoprecipitated with anti-KT3 antibody or anti-Jun antibody as sham. Immune complexes were subjected to Western blot analysis using an anti-MYC antibody conjugated with horseradish peroxidase as described above and in Roopra et al. (2004, *Id.*). These results are shown in FIG. 8C. Increasing concentrations of NADH disrupted binding of CtBP to NRSF in a dose dependent manner. Half maximal binding occurred at a physiologically relevant concentrations of ~70 nM (data not shown). These results showed that MYC-NRSF was found in the CtBP2 immune complex and thus NRSF was physically associated with CtBP2 in living cells. The Figure also shows that the amount of CtBP2 associated with NSRF decreased with increasing NADH concentration.

Figure 9:
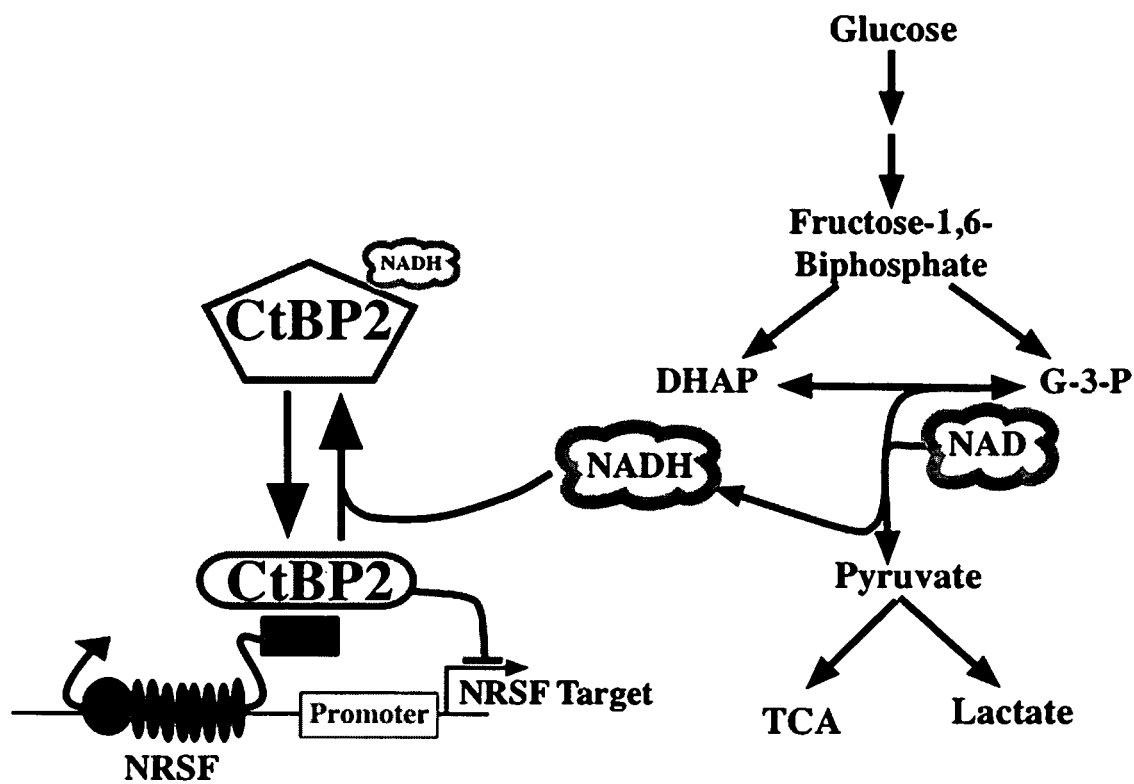
FIG. 9 is a schematic diagram illustrating a mechanism for NADH-mediated regulation of NRSE/NRSF-regulated transcription through CtBP2.

A schematic diagram of a mechanism for NADH-mediated regulation of NRSE/NRSF-regulated transcription through CtBP2 is shown in FIG. 9.

EXAMPLE 4

Figure 10A:
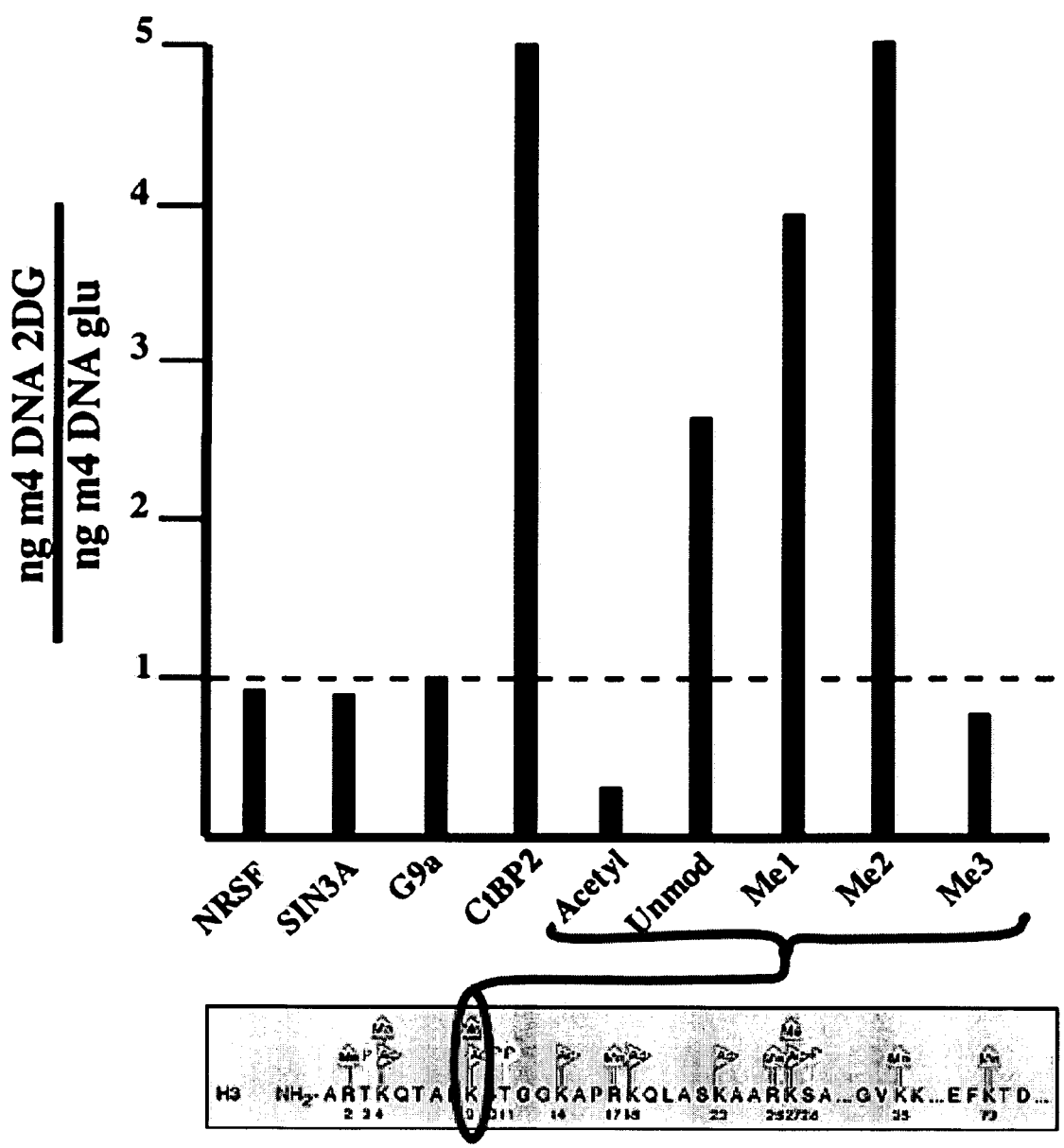
FIGS. 10A through FIG. 10C illustrate the results of experiments demonstrating that the redox charge in a cell resulting from changes in glycolysis levels influences the modification pattern of Lys9 in histone H3 (SEQ ID NO:7).
Figure 10B:
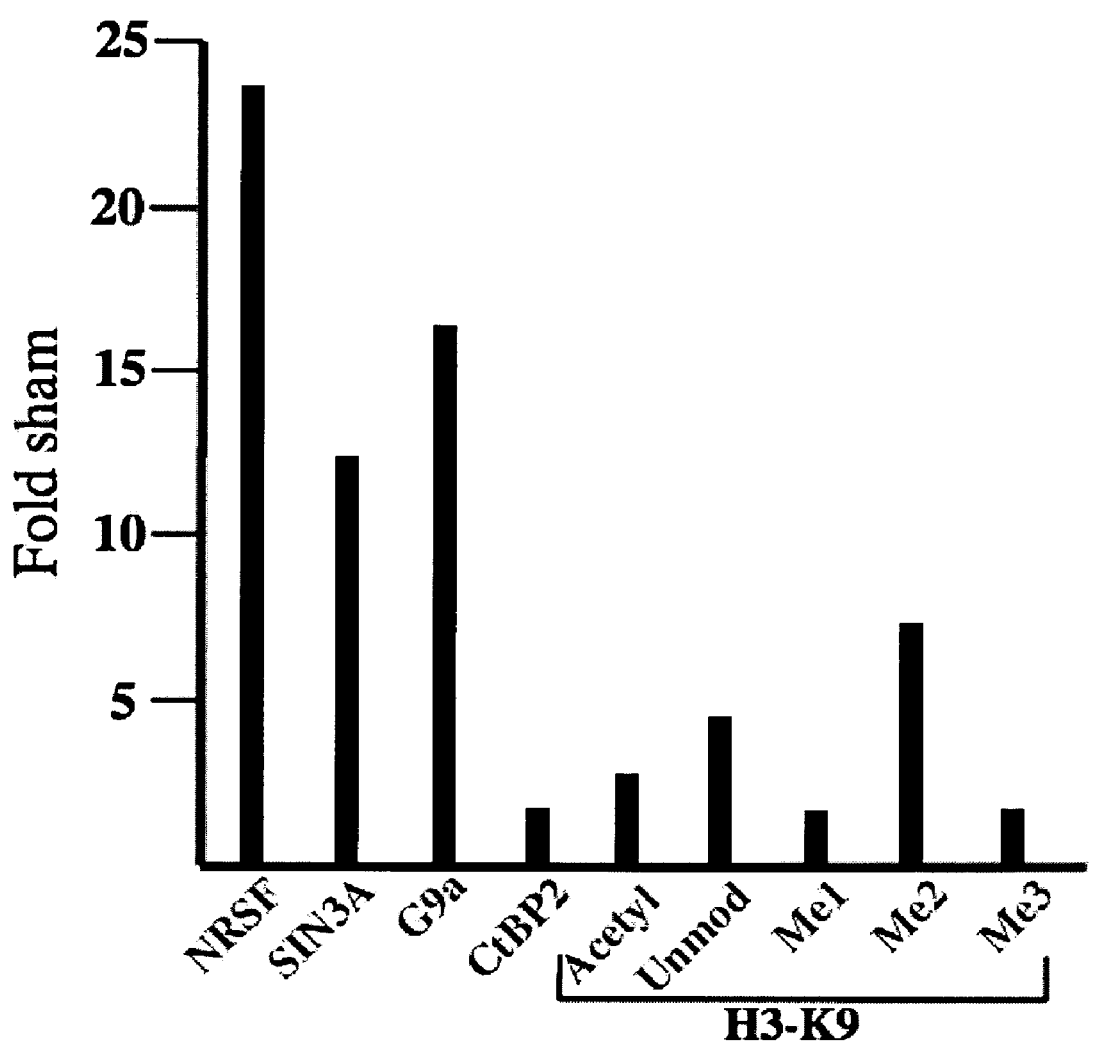
Figure 10C:
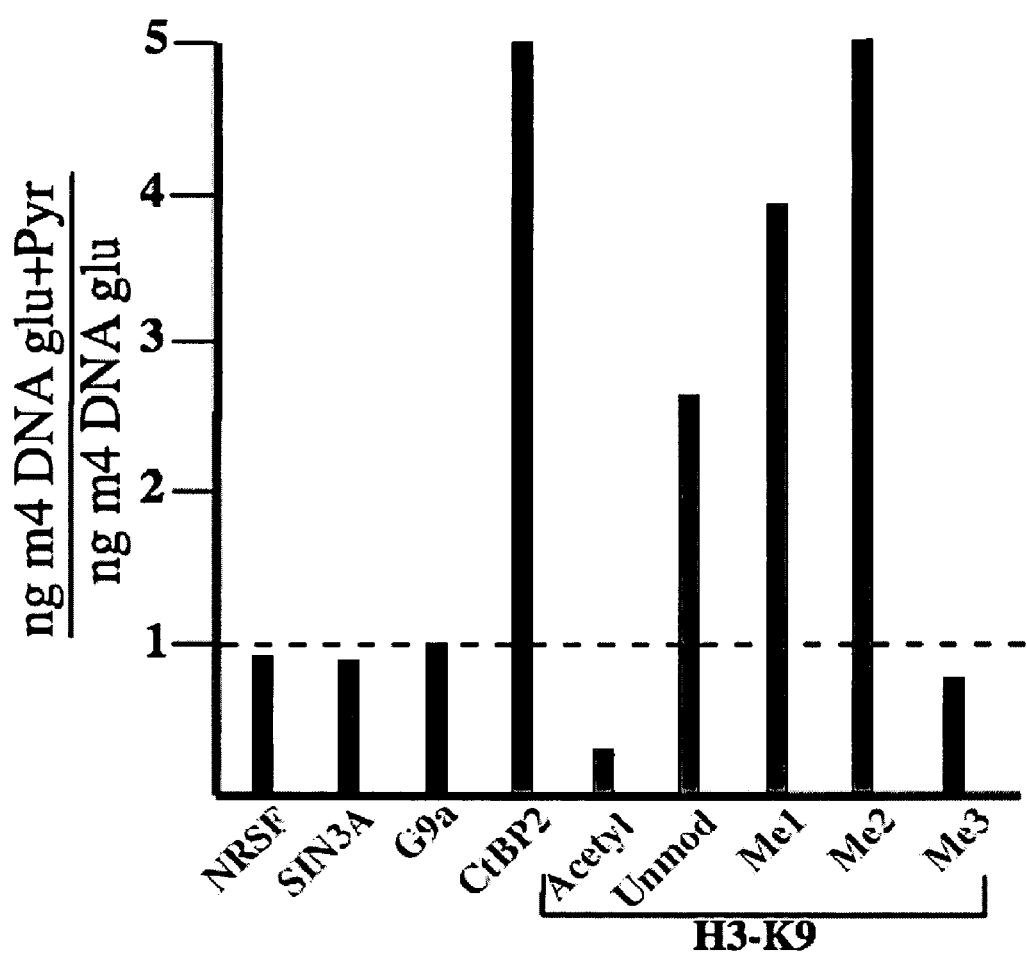

NRSF effects repression of NRSE-linked gene expression by recruiting histone deacetylases and methylases to NRSE elements of target promoters. (Timmusk & Metsis, 1994, *Neurochem Int* 25: 11-5) Thus, the effects of 2-DG on chromatin structure in the vicinity of genes whose expression was modulated by 2-DG via NRSE/NRSF was examined Histone methylation and acetylation was evaluated in NRSE/NRSF-regulated genes, wherein DNA associated with nucleosomes having these modified histone components, wherein H3 proteins having methylated or unmodified Lys$^9$ residues are associated with transcriptionally-inactive DNA, while H3 proteins acetylated at Lys$^9$ are associated with transcriptionally-active DNA. To determine whether 2-DG mediated suppression of BDNF levels was associated with a decreased level of histone H3 Lysine$^9$ acetylation, hippocampii from 2-DG treated or control rats were crosslinked with 1% formaldehyde and subjected to chromatin immunoprecipitation assays (ChIPs), performed as in Roopra et al.(2004, *Mol Cell* 14: 727-38) with an antibody specific to acetylated H3-K9. The graphs shown in FIGS. 10A through 10C show the results of experiments in which the amount (in ng) of DNA associated with nucleosomes comprising modified or unmodified H3 histone proteins was detected for an endogenous, NRSE/NRSF-regulated gene (CHRM4) in JTC-19 cells grown in the presence of 2-DG or glucose. As can be seen from the Figures, the amount of NRSF, G9a and SIN3 does not change at NRSF target genes in the presence or absence of 2-DG, a result expected because gene expression for these genes is not regulated by NRSE/NRSF. However, the amount of CtBP recruited to CHRM4, the NRSF target gene, increased 5-fold in the presence of 2-DG. This result is consistent with the effect of 2-DG to down regulate glycolysis, reduce NADH levels and thus allow increased binding of CtBP to NRSF. The Figure also shows that H3-Lys$^9$ acetylation levels were reduced at this promoter in the presence of 2-DG. This result was also consistent with the expected 2-DG effect, since acetylation is associated with transcriptional activation. The amount of unmodified (or "de-acetylated") H3K9 was also increased, which was expected since unmodified or de-acetylated H3K9 is associated with transcriptional repression. Finally, the amount of mono- and di-methyl K9 was increased, modifications also associated with increased repression. The results of these experiments demonstrated that the redox charge in a cell resulting from changes in glycolysis levels influenced the modification pattern of Lys$^9$ in histone H3.

Figure 10D:
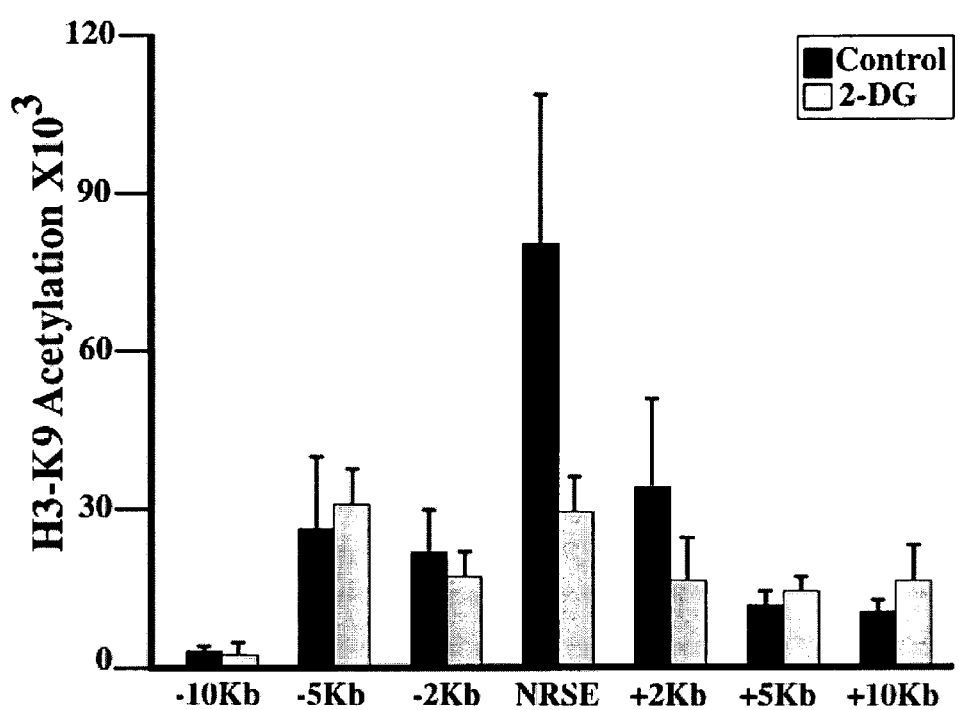
FIG. 10D is a graph showing the results of CHiP assays of ~20 kB surrounding the NRSE element in the BDNF gene. The data is plotted as the quantity of DNA specifically precipitated (pg).

ChIP assays also were performed over 20 Kb spanning the BDNF NRSE to detect deacetylated histone H3K9. In these experiments, hippocampi from rats administered 2-DG or saline for 2 weeks were subjected to CHIP with anti-H3K9-acetyl (obtained from BD-Pharmigen) or sham antibody and primers flanking BDNF NRSE or sequence 2, 5 or 10 Kb up- or downstream from the BDNF NRSE element. These results are shown in FIG. 10D, wherein the only amplicon to show marked reduction in H3K9 acetylation in 2DG-treated rats compared to controls was the NRSE element.

Figure 10E:
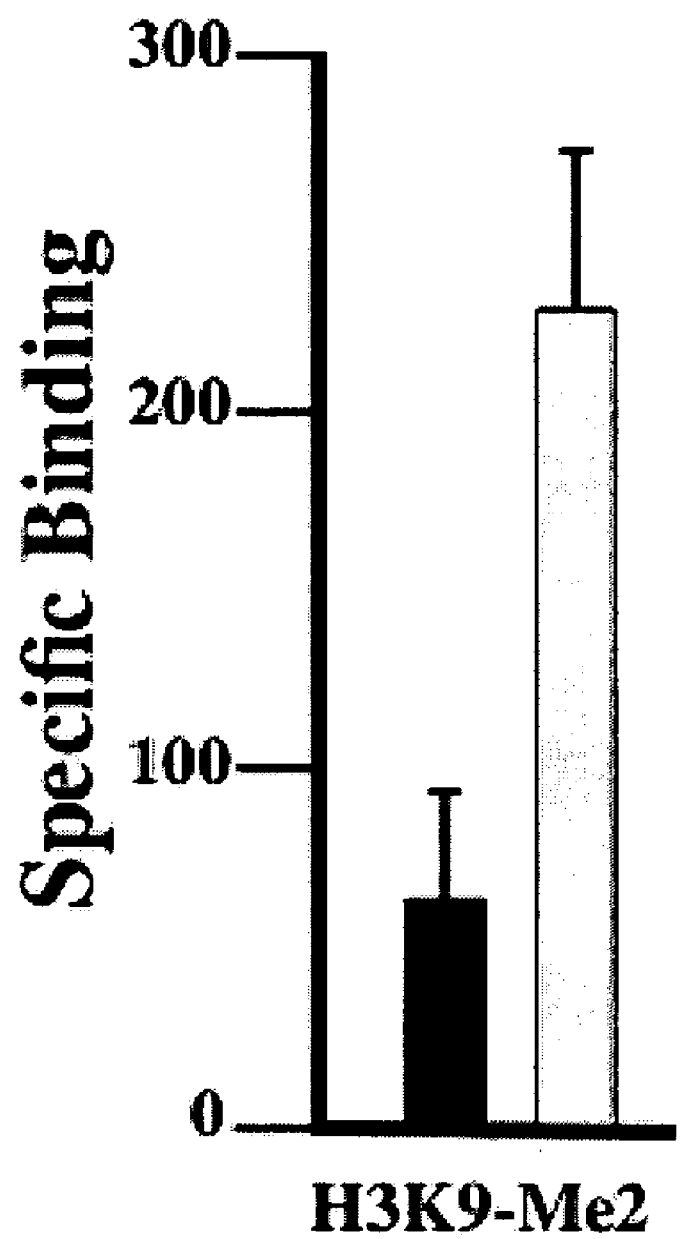
FIG. 10E is a graph showing the results of CHiP assays wherein chromatin precipitated with anti-H3K9-dimethyl or sham antibody and primers flanking the BDNF NRSE. The data is plotted as the quantity of DNA specifically precipitated (pg).

Chromatin from these experiments was immunoprecipitated with anti-H3K9-dimethyl or sham antibody and primers flanking the BDNF NRSE, showing (FIG. 10E) that there was a robust increase in H3K9 methylation status upon 2DG treatment at the BDNF NRSE, consistent with decreased BDNF expression and NRSF's known interaction with the G9a histone methylase (see, Roopra et al., 2004, *Id*. and Ballas et al., 2005, *Cell* 121: 645-57 (2005). Reduction in glycolysis decreased H3K9 acetylation and increased H3K9 dimethylation around the BDNF NRSE. These in vitro results recapitulated the chromatin alterations seen upon 2-DG administration at the hippocampal BDNF locus in vivo.

Figure 10F:
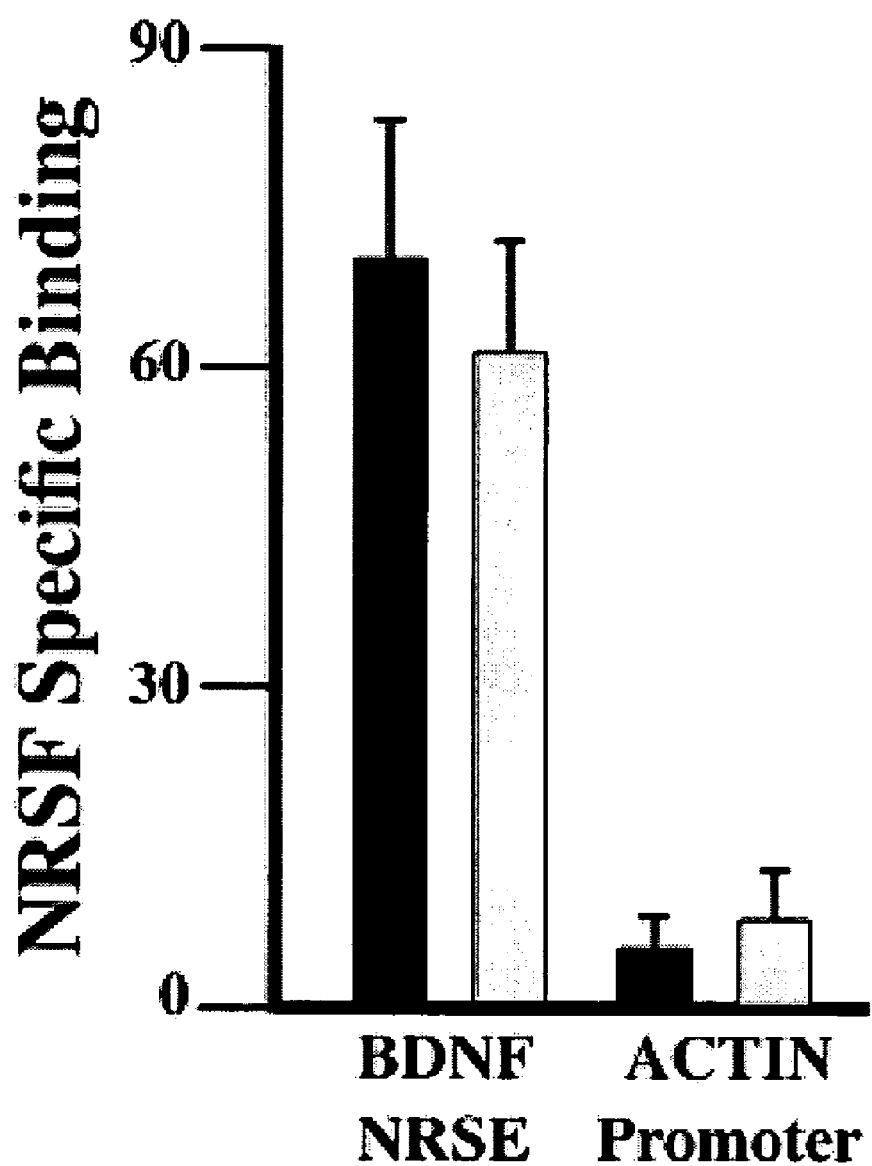
FIG. 10F is a graph showing the results of CHiP assays wherein chromatin was precipitated with anti-NRSF or sham antibody and primers flanking the BDNF or actin promoter. The data is plotted as the quantity of DNA specifically precipitated (pg).

Alternatively, when chromatin from the above experiments was precipitated with anti-NRSF or sham antibody and primers flanking the BDNF NRSE or actin promoter, specific binding was found at the NSRE element and not associated with the actin promoter. These results are shown in FIG. 10F, establishing that NRSF was bound to the BDNF NRSE in vivo but not to the actin promoter. These results further showed that NRSF binding was not affected by 2-DG administration. These results strongly suggested that the transcription factor NRSF may be mediating the down-regulation of transcription and contributing to the antiepileptic effects of 2-DG in vivo through regulation of BDNF and TrkB.

Figure 10G:
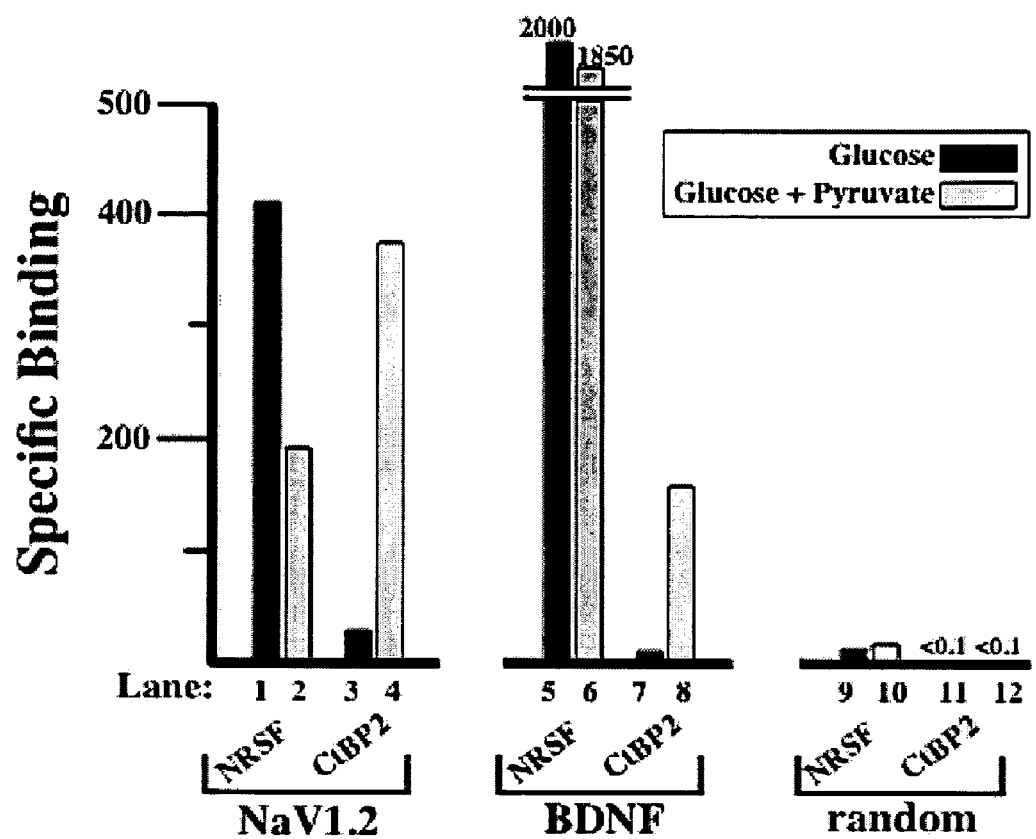
FIG. 10G shows graphs of specific binding between NRSF and CtBP in JTC-19 cells under conditions of glycolytic inhibition. Precipitated DNA was interrogated and subject to QRT-PCR with primers flanking the NRSEs of the BDNF and NaV1.2 genes or a sequence with no NRSE. Data is plotted as quantity of DNA specifically precipitated in picograms.

ChIP was also used to directly assay CtBP2 binding to NRSF target genes under conditions of glycolytic inhibition. ChIP was performed with antibodies to NRSF or CtBP2 on JTC-19 cells grown in the presence or absence of pyruvate. Addition of pyruvate to the growth media (to reduce glycolysis and thus reduce cytoplasmic/nuclear NADH) increased CtBP2 occupancy at the NaV1.2 and BDNF NRSEs (FIG. 10G). Importantly, there was no change in CtBP2 occupancy at a 'random' site lacking an NRSE, demonstrating that CtBP2 recruitment is localized to the NRSE.

Figure 10H:
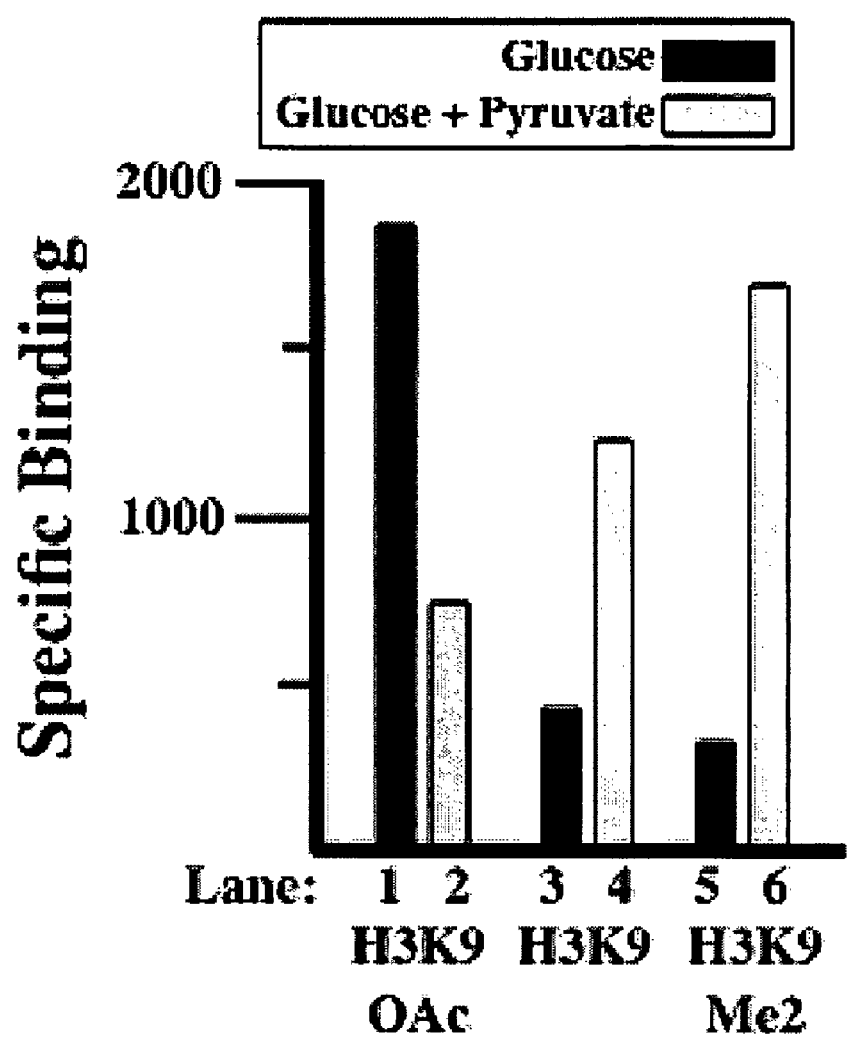
FIG. 10H is a graph showing specific binding of antibodies to acetylated, dimethylated or unmodified H3K9 in the presence and absence of glycolytic inhibition by 2-DG. ChIP was performed on JTC-19 cells as in FIG. 16D above and interrogated with primers flanking the BDNF NRSE.

To assess the impact of CtBP recruitment on chromatin status around the NRSE, we assessed the levels of acetylation and methylation at histone H3 Lysine 9 (H3K9). ChIP was performed on JTC-19 cells using antibodies to acetylated, dimethylated or unmodified H3K9 and interrogated with primers flanking the BDNF NRSE. These results are shown in FIG. 10H, wherein reductions in glycolysis decreased H3K9 acetylation and increased H3K9 dimethylation around the BDNF NRSE. These in vitro results recapitulate the chromatin alterations seen upon 2DG administration at the hippocampal BDNF locus in vivo.

Figure 10I:
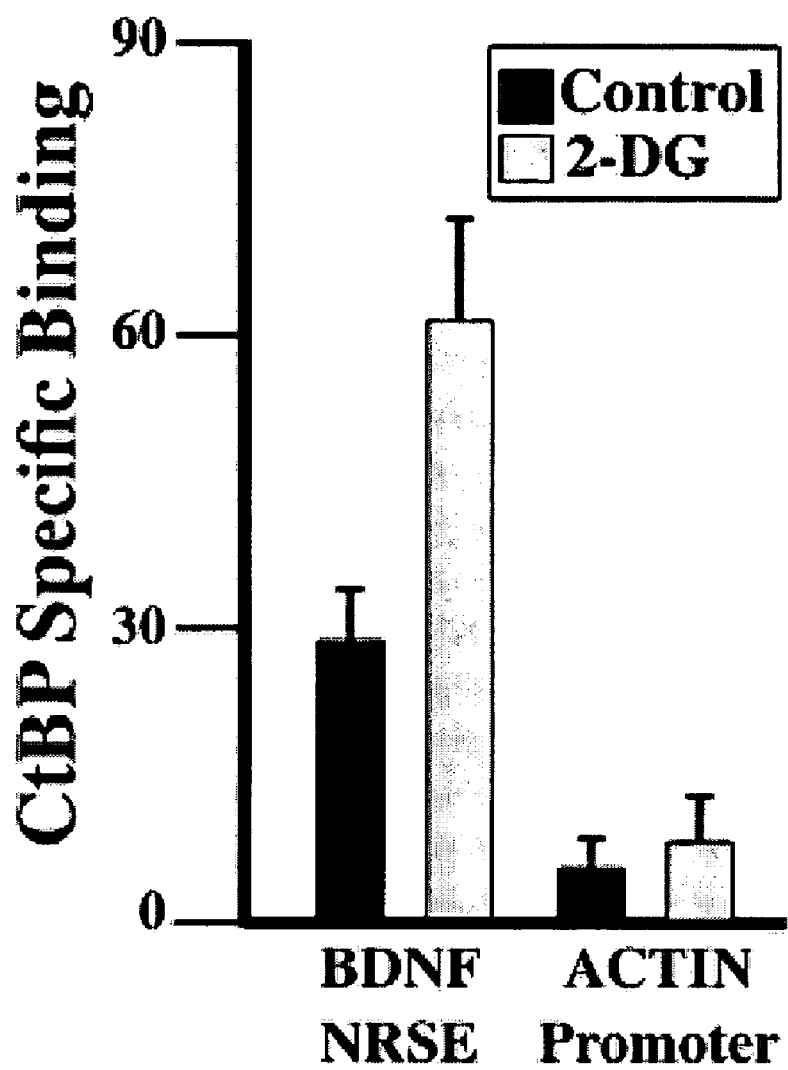
FIG. 10I is a graph of CHIP assays performed on hippocampi from rats administered 2-DG or saline for 2 weeks and using a cocktail of anti-CtBP1 and anti-CtBP2 antibody or sham antibody and primers flanking the BDNF NRSE or actin promoter. Data is plotted as quantity of DNA specifically precipitated in picograms.

The above results predicted that CtBP would be present at the BDNF NRSF binding site in rat hippocampi and that occupancy at this site should be augmented in the presence of 2-DG. To test this prediction, ChIP assays were performed using anti-CtBP antibody on chromatin isolated from 2DG-treated rats as above. Hippocampi from rats administered 2-DG or saline for 2 weeks were subjected to ChIP with a cocktail of anti-CtBP1 and anti-CtBP2 antibody or sham antibody and primers flanking the BDNF NRSE or actin promoter. FIG. 10I shows these results, wherein CtBP was present as predicted at the BDNF NRSE in rat hippocampi and that occupancy was significantly increased in rats treated with 2DG. CtBP was not detected at the actin promoter without regard to the glycolytic state of the animal, as expected for a gene not under NRSF regulatory control.

Together, these results demonstrate that glycolytic rate influences seizure threshold, and regulates expression levels of epilepsy-related genes and chromatin status in vivo. These effects are mediated via an NADH-labile recruitment of the corepressor CtBP to NRSF target genes.

Figure 11:
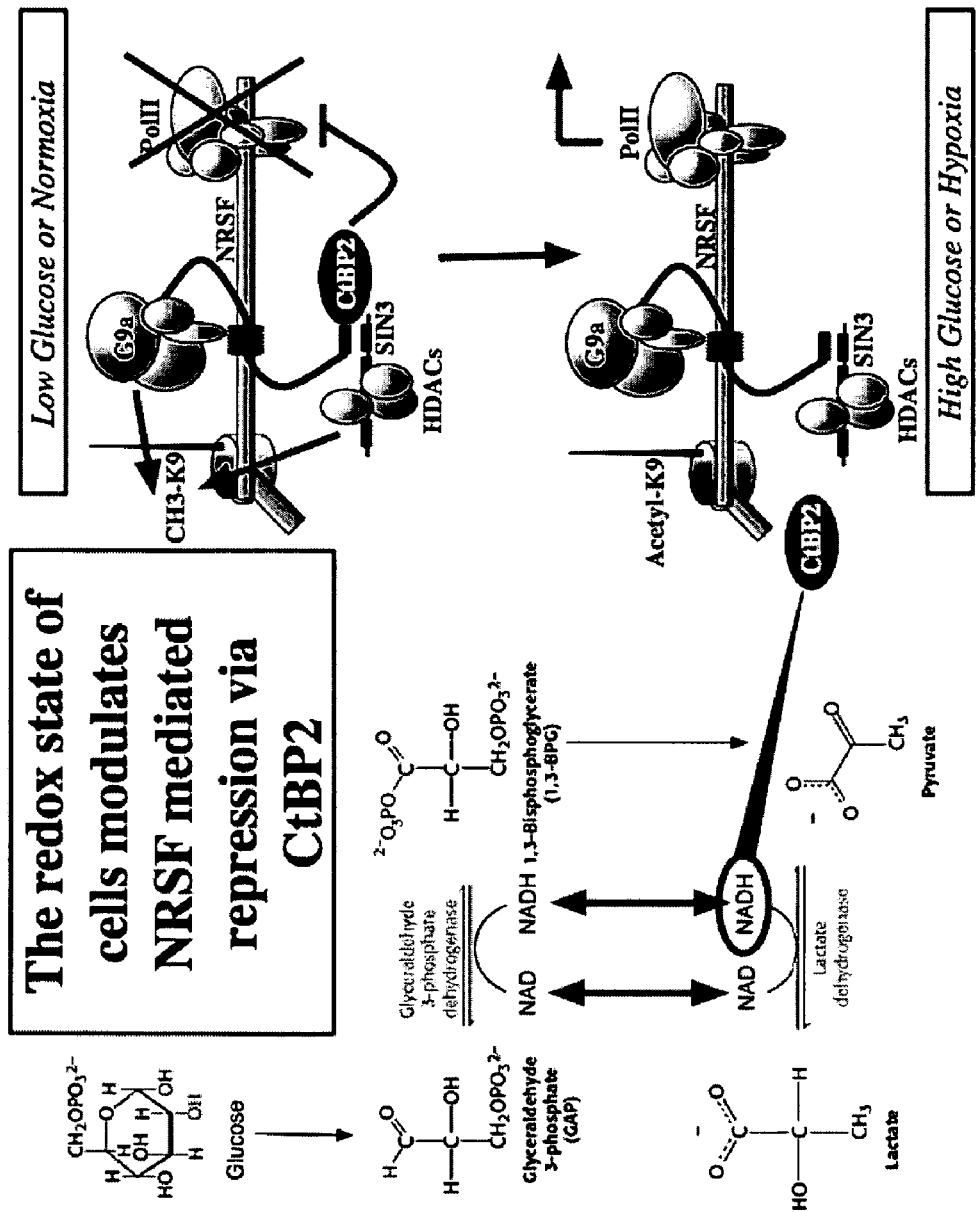
FIG. 11 is a schematic diagram illustrating how the redox charge on a cell influences transcription and histone modification mediated by the NADH-sensitive transcriptional co-repressor CtBP2. As shown in the diagram, under conditions of reduced NADH intracellular concentration that occurs under normoxic or low glucose conditions, CtBP2 associates with NRSF and inhibits transcription of NRSE/NRSF-regulated genes, and the complex also associates with G9a, which methylates Lys$^9$ of histone H3 protein in nucleosomes associated with the gene. In contrast, under high glucose or hypoxic conditions, when the intracellular concentration of NADH is increased, CtBP2 dissociates from NRSF, resulting in a loss of transcriptional repression and acetylation of Lys$^9$ in histone H3 comprising nucleosomes associated with the gene.

FIG. 11 is a schematic diagram illustrating how the redox charge on a cell influences transcription and histone modification mediated by the NADH-sensitive transcriptional co-repressor CtBP2. As shown in the diagram, under conditions of reduced NADH intracellular concentration that occurs under normoxic or low glucose conditions, CtBP2 associates with NRSF and inhibits transcription of NRSE/NRSF-regulated genes, and the complex also associates with G9a, which methylates Lys$^9$ of histone H3 protein in nucleosomes associated with the gene. In contrast, under high glucose or hypoxic conditions, when the intracellular concentration of NADH is increased, CtBP2 dissociates from NRSF, resulting in a loss of transcriptional repression and acetylation of Lys$^9$ in histone H3 comprising nucleosomes associated with the gene. These results were consistent with and support the finding that CtBP2 mediates the effects of NADH on NRSE/NRSF-regulated gene expression.

EXAMPLE 5

To investigate whether the effects of 2-DG on gene expression is evidenced in genes known to be involved in metastatic growth, the NRSF binding site (NSRE) from the mouse homolog of the human snail promoter (GenBank Accession No. NM_005985), comprising a 440 bp nucleotide sequence

```
5' GGATGCCCGTACCTTAGTGGGGCTTGCCTGGTGTACCGCAGTACCCC
AGCCTCTCAGGCAGGTCTGTGGCTTGGAGGGTACATTAGCATCTCTGAGC
TGCATGGCCACTGGGAAGATCTCTGGGTCCAGCAAAGGCAGAGGCCTGTG
AACAGGATTAGAGTCAGCACCGAGGACAGGTTTGGTGGCCAGAGCAGAGT
TCAGATCGAGTCCAAAAGGAAGAGCTGAGACCTTGGAAAATCATTGCCTT
CCCACAACGGTCACCAGAGGAAGGGGATGAGAGAAGATAACTGAACAAAG
AACATTTATATATGTTACACAAATTATATATGCATTTCATATATATATGT
AATTGTGAAATAATACATTTTTTCAAAAGGAGCCCAGAGCGTGGATTACA
GATGGCTATATGCTGCCAGATATGATTGCTGGGGAAGAACTCTG3'
``` identified as SEQ ID NO. 6 was introduced into the SV40 promoter in the plasmid vector pGL3 (available from Promega, Madison, Wis.) at the BglII and Acc65I restriction enzyme recognition sites). In pGL3. a luciferase reporter gene is under the transcriptional control of the SV40 promoter, and in the construct described herein transcription from the SV40 promoter is regulated by NRSE/NRSF. Reporter plasmids with and without the NSRE insert were transfected into HEK 293 cells (ATCC Accession No. CRL 1573 ATCC, Manassas, Va.) and the cells grown overnight in the presence of glucose with and without pyruvate, 2-DG or both pyruvate and 2DG. Transient luciferase expression was then assayed using the Dual Luciferase Reporter kit (Promega); these results are shown in FIG. 12.

Figure 12:
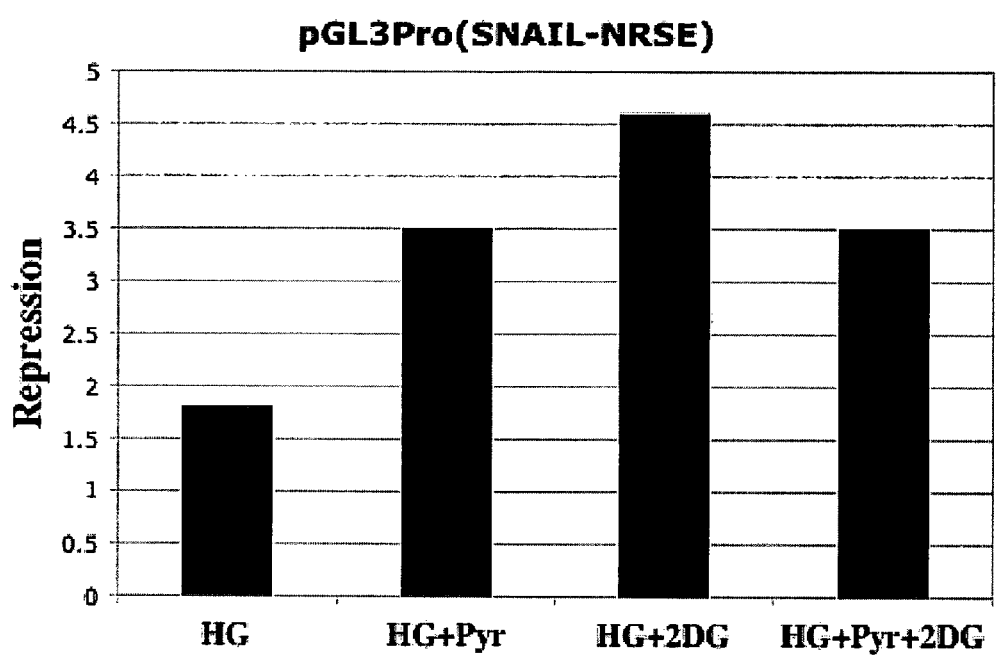
FIG. 12 is a graph showing repression of expression of a reporter gene using an SV40 promoter with or without the NRSF binding site from the human snail promoter. HG=glucose; Pyr=pyruvate; 2-DG=2-deoxyglucose.

The relative amount of luciferase expression is shown in FIG. 12, where each bar in the graph represents the ratio of SV40-driven expression to NRSE/SV40 expression in the presence of glucose alone (HG) (as a positive control), glucose+pyruvate (HG+Pyr), glucose+2-DG, or glucose+pyruvate and 2-DG (HG+Pyr+2-DG). These results showed that under conditions where glycolysis is inhibited (i.e., in the presence of pyruvate or 2-DG or both), reporter gene expression is decreased. These results are consistent with other evidence set forth herein that inhibition of glycolysis induces repression of gene expression for genes whose expression is regulated by NRSE/NRSF.

The disclosures of all references cited herein are explicitly incorporated by reference in their entirety.

It should be understood that the foregoing disclosure emphasizes certain specific embodiments of the invention and that all modifications or alternatives equivalent thereto are within the spirit and scope of the invention as set forth in the appended claims.

TABLE 1

Therapeutic applications of 2DG

| change in expression | change p-value | gene | potential disease impact | detailed description |
|---|---|---|---|---|
| D | 0.999886 | insulin-like growth factor II (somatomedin A) | growth | gb: NM_031511.1/DB_XREF = gi: |
| D | 0.999998 | transthyretin (prealbumin, amyloidosis type I) | injury amyloid neuropathy | gb: NM_012681.1/DB_XREF = gi: |
| D | 0.999998 | insulin-like growth factor binding protein 2 | ? Growth/reduced atherosclerosis | gb: NM_013122.1/DB_XREF = gi: |
| D | 0.999998 | carbonic anhydrase 2 | epilepsy | gb: NM_019291.1/DB_XREF = gi: |
| D | 0.999932 | solute carrier family 4, member 2, anionexchange protein 2 | epilepsy | gb: NM_017048.1/DB_XREF = gi: |
| D | 0.999998 | Myelin-associatedOligodendrocytic BasicProtein | MS | gb: X90402.1/DB_XREF = gi: |
| D | 0.999034 | neurexin 3 | epilepsy growth regen/deg | gb: NM_053817.1/DB_XREF = gi: |
| D | 0.998664 | potassium channel gene 1 | epilepsy | gb: NM_012856.1/DB_XREF = gi: |
| D | 0.999833 | brain derived neurotrophic factor | epilepsy, memory, CNS injury, cancer | gb: NM_012513.1/DB_XREF = gi: |
| D | 0.999965 | midkine | axon growth | gb: NM_030859.1/DB_XREF = gi: |
| D | 0.999693 | ceramide UDP-galactosyltransferase | growth | gb: L21698.1/DB_XREF = gi: 4376 |
| D | 0.999899 | glutamate transporter EAAC1 interacting protein | CNS injury | gb: M26161.1/DB_XREF = gi: 206 |
| D | 0.999811 | GABA-BR1a receptor | epilepsy | gb: BI284739/DB_XREF = gi: 149 |
| D | 0.999948 | brain lipid binding protein | brain injury deg | gb: NM_030832.1/DB_XREF = gi: 1929 |
| D | 0.998168 | MOBP (myelin-associated oligodendrocytic basic protein) | MS | gb: D28110.1/DB_XREF = gi: 644 |
| D | 0.999562 | P-glycoprotein | multidrug transporter; epilepsy, chemotherapy | gb: AF286167.1/DB_XREF = gi: 1 |
| D | 0.999034 | potassium channel protein | epilepsy | gb: NM_023972.1/DB_XREF = gi: 206 |
| D | 0.999727 | LPS-induced TNF-alpha factor | injury, degeneration, cancer | gb: Y10369.1/DB_XREF = gi: 1929 |
| D | 0.998923 | soluble fibroblast growth factor receptor IIIb | growth epilepsy | gb: AJ312745.1/DB_XREF = gi: 13 |
| D | 0.999811 | ESTs, Weakly similar to CALM_HUMAN CALMODULIN | CNS injury | gb: BG663128/DB_XREF = gi: 138 |
| D | 0.998514 | ESTs, Similar to CAHE MOUSE CARBONIC ANHYDRASE XIV PRECURSOR | epilepsy | gb: BI289989/DB_XREF = gi: 149 |
| D | 0.999932 | ESTs, Weakly similar to TANK_MOUSE TRAF-ASSOCIATED NF-KAPPA-B ACTIVATOR (TRAF- | injury | gb: AA818055/DB_XREF = gi: 419 |
| D | 0.999308 | Tissue inhibitor of metalloproteinase 3 | injury, degeneration, ?increase mets | gb: AA893169/DB_XREF = gi: 413 |
| D | 0.999998 | ESTs, Highly similar to OTX2_RAT HOMEOBOX PROTEIN OTX2 | growth response | gb: BG374268/DB_XREF = gi: 132 |
| D | 0.999973 | ESTs, Weakly similar to FZD2_RAT Frizzled 2 precursor (Frizzled-2) | ? | gb: BG374415/DB_XREF = gi: 132 |
| D | 0.999998 | ESTs, Weakly similar to CXA9 RAT GAP JUNCTION ALPHA-9 PROTEIN | epilepsy | gb: AI144646/DB_XREF = gi: 3666 |
| D | 0.999987 | carbonic anhydrase 2 | epilepsy | gb: AI408948/DB_XREF = gi: 4252 |
| D | 0.999932 | developmentally regulated protein TPO1 | ? | gb: NM_133395.1/DB_XREF = gi: |
| D | 0.999811 | solute carrier 16 (monocarboxylic acidtransporter) | ? | gb: NM_012716.1/DB_XREF = gi: |
| D | 0.999932 | myelin basic protein | MS vs epilepsy | gb: NM_017026.1/DB_XREF = gi: |
| D | 0.999965 | GABA B receptor 1 g | epilepsy | gb: AF312319.1/DB_XREF = gi: 1 |
| D | 0.998799 | ESTs, Weakly similar to AMYLOID-LIKE PROTEIN 2 PRECURSOR | alzheimers | gb: AI412117/DB_XREF = gi: 4255 |
| D | 0.999811 | ESTs, Moderately similar to CADHERIN-6 PRECURSOR | injury response cancer | gb: BI296340/DB_XREF = gi: 1496 |
| D | 0.999987 | ESTs, Weakly similar to monocarboxylate transporter homologue MCT6 | glutamate handling | gb: BI289867/DB_XREF = gi: 149 |
| D | 0.999811 | Myelin oligodendrocyte glycoprotein (Mog) | MS, axon guidance | gb: NM_022668.1/DB_XREF = gi: |
| D | 0.999998 | Tspan-2 protein | ? | gb: NM_022589.1/DB_XREF = gi: |
| D | 0.999811 | A disintegrin and metalloprotease domain (ADAM) 10 | growth cancer | gb: BI300565/DB_XREF = gi: 1497 |
| D | 0.999727 | ESTs, Highly similar to A49128 cell-fate determining gene Notch2 protein | injury response cancer | gb: AI011448/DB_XREF = gi: 4133 |
| D | 0.999759 | Heat shock 27 kDa protein | injury deg | gb: AI104388/DB_XREF = gi: 370 |
| D | 0.998923 | ESTs, similar to CA-CALMODULIN-DEPENDENT PROT KINASE II ALPHA | injury | gb: BE107291/DB_XREF = gi: 849 |
| D | 0.998168 | vimentin | injury epilepsy | gb: NM_031140.1/DB_XREF = gi: 138 |
| I | 0.000189 | ESTs, similar KFMS_RAT MACROPHAGE COL STIM FACTOR I RECEPTOR PRECURSOR | deg injury | gb: BI285793/DB_XREF = gi: 1493 |
| I | 0.000114 | ESTs, similar to HS9B_RAT HEAT SHOCK PROTEIN HSP 90-BETA | | gb: BG67152/1/DB_XREF = gi: 138 |
| I | 0.000046 | protein kinase C and casein kinase substrate in neurons | injury | gb: NM_017294.1/DB_XREF = gi |
| I | 0.000023 | huntingtin-associated protein interacting protein | Huntingtons | gb: NM_032062.1/DB_XREF = gi |
| I | 0.000002 | androgen receptor-related apoptosis-associatedprotein CBL27 | neuroprotective Alz | gb: AF275151.1/DB_XREF = gi: 9 |

TABLE 1-continued

Therapeutic applications of 2DG

| change in expression | change p-value | gene | potential disease impact | detailed description |
|---|---|---|---|---|
| I | 0.000027 | sodium bicarbonate cotransporter | ? Epilepsy | gb: AF210250.1/DB_XREF = gi: 6 |
| I | 0.001201 | sodium bicarbonate cotransporter | ? Epilepsy | gb: AF210250.1/DB_XREF = gi: 6 |
| I | 0.001201 | CaM kinase II gamma | injury | gb: NM_133605.1/DB_XREF = gi |
| I | 0.000307 | Signal transducer and activator of transcription 3 | ? | gb: BE113920/DB_XREF = gi: 850 |
| I | 0.000114 | CaM-kinase II inhibitor alpha | injury | gb: AA858621/DB_XREF = gi: 422 |
| I | 0.000189 | CaM-kinase II inhibitor alpha | injury | gb: AA858621/DB_XREF = gi: 422 |
| I | 0.000189 | ESTs similar to JC7218 giia maturation factor-gamma | injury response | gb: BG666787/DB_XREF = gi: 138 |
| I | 0.000492 | ESTs, similar to Knueppel-like Basic transcription element binding prot 3 | | gb: AI454932/DB_XREF = gi: 429 |
| I | 0.000114 | ESTs, similar to CBP MOUSE CREB-BINDING PROTEIN | | gb: BM389207/DB_XREF = gi: 18 |
| I | 0.00013 | ESTs, similar to CBP MOUSE CREB-BINDING PROTEIN | | gb: BM389207/DB_XREF = gi: 18 |
| I | 0.00013 | ESTs, similar to FXO1 MOUSE FORKHEAD PROTEIN O1A | | gb: BI295511/DB_XREF = gi: 1495 |
| I | 0.00013 | ESTs, similar to Bone morphogenetic protein receptor type II precursor | ? Glial prolif activator growth | gb: BE118651/DB_XREF = gi: 851 |
| I | 0.00013 | ESTs, Weakly similar to BD3 MOUSE BRAIN PROTEIN D3 | ? | gb: AI227829/DB_XREF = gi: 381 |
| I | 0.001832 | ESTs, Weakly similar to ataxin 2 binding protein 1; | deg injury | gb: BG380409/DB_XREF = gi: 133 |
| I | 0.00002 | ESTs, Weakly similar to ataxin 2 binding protein 1; | deg injury | gb: BG380409/DB_XREF = gi: 133 |
| I | 0.00002 | synaptotagmin IV | epilepsy growth | gb: L38247.1/DB_XREF = gi: 5983 |
| I | 0.00004 | ESTs similar to HS9B RAT HEAT SHOCK PROT HSP 90-BETA | injury deg | gb: BG671521/DB_XREF = gi: 138 |
| I | 0.000114 | ESTs similar to FKB5 MOUSE 51 KDA FK506-BINDING PROTEIN | ? injury | gb: AW534837/DB_XREF = gi: 71 |
| I | 0.000147 | CaM-kinase II inhibitor alpha | injury | gb: BE111167/DB_XREF = gi: 850 |
| I | 0.001077 | ESTs similar to FKB5 MOUSE 51 KDA FK506-BINDING PROTEIN | ? Growth cancer | gb: BE107795/DB_XREF = gi: 849 |
| I | 0.000865 | ESTs similar to FKB5 MOUSE 51 KDA FK506-BINDING PROTEIN | ? injury | gb: BI284255/DB_XREF = gi: 149 |
| I | 0.001336 | ESTs similar to A42915 type II cAMP-dependent prot kinase RII anchoring protein | injury | gb: AW526712/DB_XREF = gi: 71 |
| I | 0.000692 | EST similar to SX10 RAT TRANSCRIPTION FACTOR SOX-10 | | gb: AI454332/DB_XREF = gi: 4292 |
| I | 0.000035 | crystallin, alpha polypeptide 2 | neuropathy denervation | gb: NM_012935.1/DB_XREF = gi |
| I | 0.00002 | disintegrin and metalloproteinase with thrombospondin motifs 1 (ADAMTS-1) | ? injury deg cancer mets | gb: NM_024400.1/DB_XREF = gi |
| MD | 0.99751 | L-type calcium channel alpha2delta subunit | epilepsy | gb: AF400662.1/DB_XREF = gi: 1 |
| MD | 0.99775 | Superoxide dismutase 2, mitochondrial | ? Worsen deg injury ALS | gb: BG671549/DB_XREF = gi: 138 |
| MD | 0.99751 | EST similar to plasminogen activator inhibitor 2 type A | injury response epilepsy | gb: BF411331/DB_XREF = gi: 113 |
| MD | 0.99751 | ESTs, Weakly similar to PN0509 integrin beta-3 chain | growth ?cancer | gb: AI070686/DB_XREF = gi: 339 |
| MD | 0.99775 | thyrotropin releasing hormone receptor | growth | gb: NM_013047.1/DB_XREF = gi |
| MI | 0.00249 | metabotropic glutamate receptor type 1 | epilepsy | gb: Y18810.1/DB_XREF = gi: 553 |
| MI | 0.00225 | Tumor necrosis factor (ligand) | worsen injury deg | gb: NM_012908.1/DB_XREF = gi |
| MI | 0.00249 | Na-K transporting ATPase gamma chain | epilepsy | gb: AF129400.1/DB_XREF = gi: 4 |

What we claim is:

1. A method for reducing gene expression in a mammalian cell for genes operably linked to an Neuron Restrictive Silencing Element (NRSE) that is recognized by an Neuron-Restrictive Silencing Factor (NRSF) transcriptional repressor, comprising the step of changing reduced nicotinamide adenine dinucleotide (NADH) concentrations in the cell, wherein gene expression for genes operably linked to an NRSE element is decreased when the amount of NADH in the cell is reduced, and the amount of NADH in the cell is decreased by inhibiting enzymatic activity of a glycolytic enzyme wherein the glycolytic enzyme is hexokinase (E.C. 2.7.1.1), glucokinase (E.C. 2.7.1.2), glucose-6-phosphate isomerase (E.C. 5.3.1.9), 6-phosphofructo-1-kinase (E.C. 2.7.1.11), fructose bisphosphate aldolase (E.C. 4.1.2.13), glyceraldehyde-3-phosphate dehydrogenase (E.C.1.2.1.12), triose phosphate isomerase (E.C. 5.3.1.1), phosphoglycerate kinase (E.C. 2.7.2.3), phosphoglyceromutase (E.C. 5.4.2.1), or pyruvate kinase (E.C. 2.7.1.40).

2. The method of claim 1 wherein the glycolytic enzyme is glucose-6-phosphate isomerase (E.C. 5.3.1.9).

3. The method of claim 2, wherein glucose-6-phosphate isomerase (E.C. 5.3.1.9) is inhibited by contacting the cell with 2-deoxy-D-glucose, 3-deoxy-D-glucose, 4-deoxy-D glucose, 5-deoxy-D-glucose, 2, n-deoxy-D-glucose, where n=3-5, n, m-deoxy-D-glucose, where n=2-5 and m=integers from 2-5 excluding n, sugars that can be metabolized into 2-DG, including 2-deoxy-D-galactose, halogenated and other conjugated derivatives of deoxy sugars, including fluoro-2-deoxy-D-glucose, conjugated deoxy sugars that are metabolized to 2-DG, or iodoacetate.

4. The method of claim 3, wherein glucose-6-phosphate isomerase (E.C. 5.3.1.9) is inhibited by contacting the cell with 2-deoxy-D-glucose.

* * * * *